(12) United States Patent
Lehmann et al.

(10) Patent No.: US 7,382,819 B2
(45) Date of Patent: Jun. 3, 2008

(54) METHOD OF MONITORING PRESSURE OF A GAS SPECIES AND APPARATUS TO DO SO

(75) Inventors: Martin Lehmann, Obere Fahrnbuhlstasse 1 CH-5610, Wohlen AG (CH); Jean-Noel Fehr, Pre-du-Chateau (CH); Martin Liechti, Tscharnerstrasse (CH); Urban Schnell, St-Jodelweg (CH)

(73) Assignee: Martin Lehmann, Wohlen AG (CH)

( * ) Notice: Subject to any disclaimer, the term of this patent is extended or adjusted under 35 U.S.C. 154(b) by 0 days.

(21) Appl. No.: 11/707,090

(22) Filed: Feb. 16, 2007

(65) Prior Publication Data

US 2007/0144265 A1 Jun. 28, 2007

Related U.S. Application Data

(62) Division of application No. 10/894,309, filed on Jul. 20, 2004, now Pat. No. 7,222,537.

(51) Int. Cl.
*G01L 7/00* (2006.01)
(52) U.S. Cl. .............................. 373/756; 29/592; 29/437
(58) Field of Classification Search ................. 73/756; 29/592; 356/437
See application file for complete search history.

(56) References Cited

U.S. PATENT DOCUMENTS

| 4,123,160 A | 10/1978 | Caputo et al. |
| 4,492,469 A | 1/1985 | Fujimori |
| 4,493,553 A | 1/1985 | Korb et al. |

(Continued)

FOREIGN PATENT DOCUMENTS

EP   1 450 139 A2   8/2004

(Continued)

OTHER PUBLICATIONS

L.C. Philippe and R.K. Hanson, Laser diode wavelength-modulation spectroscopy for simultaneous measurement of temperature, pressure, and velocity in shock-heated oxygen flows, Applied Optics, vol. 32, Oct. 20, 1993, No. 30, Washington, US.

(Continued)

*Primary Examiner*—Andre J. Allen
(74) *Attorney, Agent, or Firm*—Antonelli, Terry, Stout & Kraus, LLP.

(57) ABSTRACT

A method of monitoring pressure of a gas species up to at most a predetermined maximum pressure value is disclosed. The method includes exposing the gas species to transmission of laser light, periodically modulating the wavelength of the laser light over a wavelength band including at least one absorption line of the gas species, optoelectrically converting the transmitted laser light, thereby generating an electric output signal, performing at least one of first filtering the electric output signal with a filter characteristic having a lower cut-off frequency not lower than a transition frequency and of second filtering the electric output signal with a bandpass filter characteristic having an upper cut-off frequency not higher than the transition frequency and a lower cut-off frequency above the modulation frequency of the periodic wavelength modulation. The output of at least one of the filterings is evaluated as a pressure indicative signal.

30 Claims, 24 Drawing Sheets

U.S. PATENT DOCUMENTS

Figure 1:
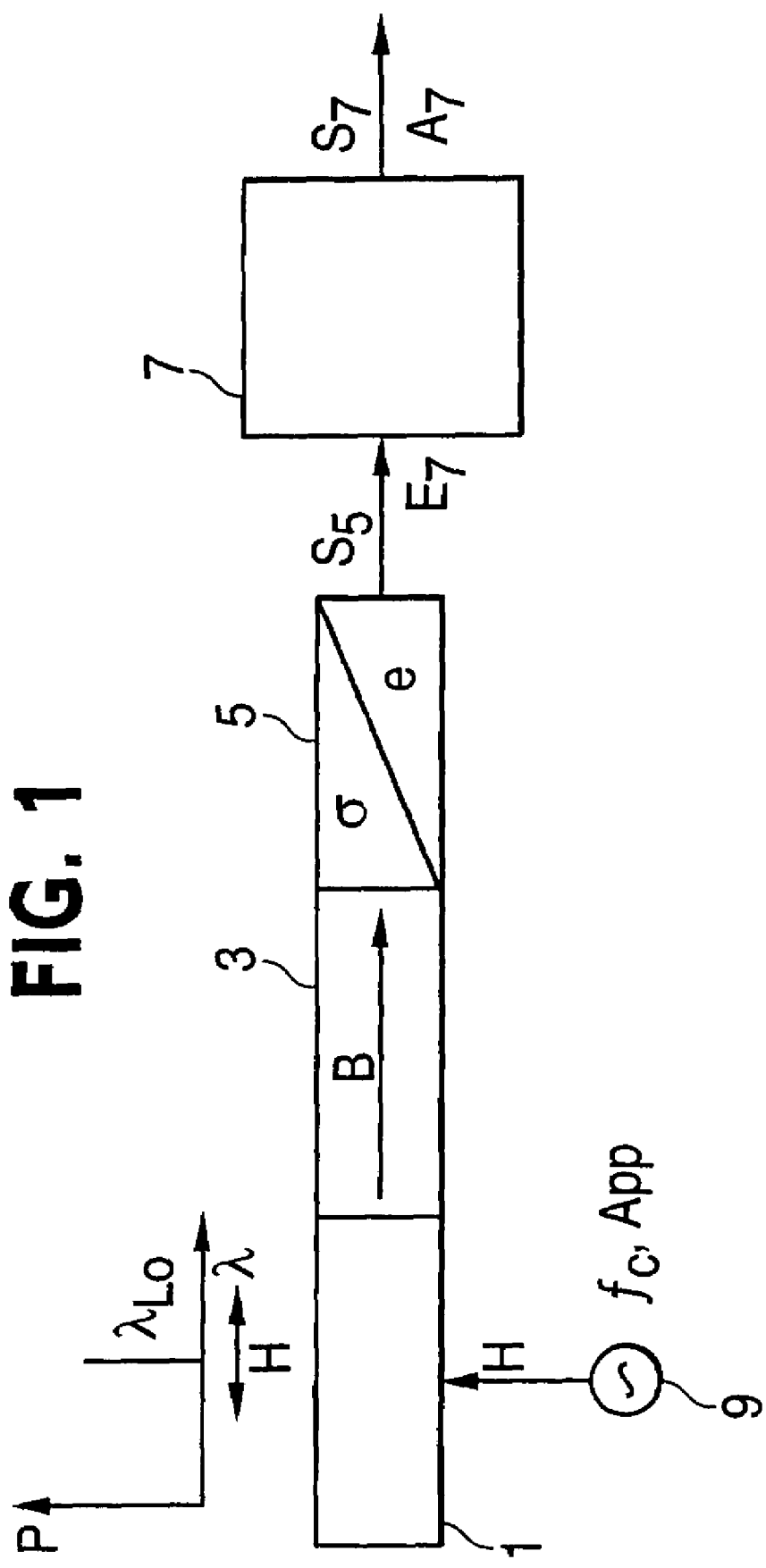

| | | | |
|---|---|---|---|
| 4,934,816 A | * | 6/1990 | Silver et al. ............... 356/409 |
| 4,937,448 A | * | 6/1990 | Mantz et al. ............... 250/343 |
| 5,202,570 A | * | 4/1993 | Tanaka et al. ............... 250/575 |
| 5,636,035 A | | 6/1997 | Whittaker et al. |
| 5,637,872 A | | 6/1997 | Tulip |
| 5,640,245 A | | 6/1997 | Zybin et al. |
| 6,356,350 B1 | | 3/2002 | Silver et al. |
| 6,639,678 B1 | | 10/2003 | Veale |
| 7,067,323 B2 | | 6/2006 | Veale et al. |
| 2001/0015408 A1 | | 8/2001 | Stock |
| 2005/0022603 A1 | | 2/2005 | Lehmann et al. |

FOREIGN PATENT DOCUMENTS

| | | |
|---|---|---|
| FR | 2 735 236 | 12/1996 |
| WO | WO 2005/040753 A2 | 5/2005 |

OTHER PUBLICATIONS

European Search Report dated Apr. 6, 2005 from Application No. EP 05 00 0293.

Hans P. Zappe, et al.; Narrow-linewidth vertical-cavity surface-emitting lasers for oxygen detection; May 20, 2000; pp. 2475-2479.

* cited by examiner

METHOD OF MONITORING PRESSURE OF A GAS SPECIES AND APPARATUS TO DO SO

This application is a divisional application of application Ser. No. 10/894,309 filed Jul. 20, 2004 now U.S. Pat. No. 7,222,537, which also relates to continuation in part application Ser. No. 11/152,236 filed Jun. 15, 2005, the disclosure of which is hereby incorporated by reference.

The present invention is directed on a novel method and apparatus and on various embodiments thereof for monitoring pressure of a gas species. It resulted from the need of rapidly monitoring oxygen content in transparent closed containers, as of glass or plastic material vials, e.g. for medical appliances.

Under a first aspect a first embodiment of the method according to the present invention of monitoring of a gas species up to at most a predetermined maximum pressure value, such method comprises exposing the gas species to transmission of laser light;
periodically modulating the wavelength of the laser light over a wavelength band which includes at least one absorption line of the gas species;
optoelectrically converting the transmitted laser light, thereby generating an electric output and it further comprises at least one of first filtering the electric output signal of converting with a filter characteristic which has a lower cut-off frequency which is not lower than a transition frequency and of
second filtering the electric output signal of the conversion with a band pass filter characteristic which has an upper cut-off frequency which is not higher than the transition frequency and with a lower cut-off frequency above modulation frequency of the periodic wavelength modulation.

Thereby, the transition frequency in the spectrum of the electric output signal of conversion is determined there where the caustic function of the pressure-dependent spectrum envelopes of the addressed output electric signal touches the envelope of the spectrum at the maximum pressure.

The output of the addressed at least one filtering is evaluated as a pressure indicative signal.

In one embodiment both, namely first and second filtering, are performed.

In one embodiment the first filtering is performed as band pass filtering.

In one embodiment the first filtering is performed with a lower cut-off frequency which is higher than the addressed transition frequency.

In another embodiment the first filtering is performed as band pass filtering and there is determined a filter frequency above the lower cut-off frequency of the addressed first filtering there where the derivatives of spectral amplitude vs. pressure of the electric output signal of the conversion at least approximately accord with a desired characteristic. Then band pass first filtering is performed with the determined filter frequency as band pass center frequency.

In a further embodiment the first filtering is performed as band pass filtering and bandwidth of this band pass filtering is selected with the target of achieving a desired signal to noise ratio.

Still in a further embodiment the first filtering is performed as a band pass filtering and a desired sensitivity of the output signal of the band pass first filtering is realized under consideration of noise in that the followings steps are performed once or more than one time in a looping manner:

(a) A filter frequency is determined above the lower cut-off frequency of the first filtering there where the derivative of spectral amplitude vs. pressure of the electric output signal of conversion at least approximately accords with a desired characteristic. Band pass center frequency of the addressed band pass first filtering is established at the filter frequency thus determined.

(b) The bandwidth of the band pass first filtering is designed for a desired signal to noise ratio.

In a further embodiment the method according to the present invention comprises selecting the upper cut-off frequency of the second filtering below the addressed transition frequency.

Still in a further embodiment of the method according to the present invention the second filtering is performed with a center frequency there where the derivative of spectral amplitude vs. pressure of the electric output signal at least approximately accords with a desired characteristic.

Still in a further embodiment the second filtering is performed with a bandwidth selected for a desired signal to noise ratio.

In a further embodiment the second filtering is performed, thereby realizing a desired sensitivity of an output signal of the addressed second filtering under consideration of noise by performing the following steps subsequently once or in a looping manner more than one time:

(a) Determining a center frequency of the second filtering there where the derivative of spectral amplitude vs. pressure of the electric output signal of conversion at least approximately accords with a desired characteristic and
(b) tailoring bandwidth of the second filtering for a desired signal to noise ratio.

Under a second aspect of the present invention there is established the method of monitoring pressure of a gas species within a predetermined pressure range, namely between a maximum pressure value and a minimum pressure value. This latter method comprises exposing the gas species to transmission of laser light;
periodically modulating the wavelength of the laser light over a wavelength band which includes at least one absorption line of the gas species;
optoelectrically converting the transmitted laser light, thereby generating an electric output signal;
then at least one of the following steps is performed
first filtering of the electric output signal of conversion with a filter characteristic which has a lower cut-off frequency not lower than a transition frequency and
second filtering of the electric output signal of conversion with a band pass filter characteristic which has an upper cut-off frequency which is not higher than the transition frequency and with a lower cut-off frequency which is above modulation frequency of the periodic wavelength modulation.

Thereby, the addressed transition frequency in this case is determined in the spectrum of the electric output signal there where the spectrum envelopes of the electric output signal at the minimum and at the maximum pressure values intersect.

Then the output signal of at least one of the addressed first and second filtering is evaluated as a pressure indicative signal.

In one embodiment both the first and second filtering is performed under the second aspect.

In a further embodiment under the second aspect the first filtering is performed as band pass filtering.

Under another mode of the second aspect of the present invention the first filtering is performed with a lower cut-off frequency which is higher than the transition frequency.

Under the second aspect another embodiment comprises performing the first filtering as band pass filtering between the transition frequency and a noise limit frequency. The noise limit frequency is thereby defined there where noise energy of the electric output signal of conversion equals signal energy of that electric output signal at the predetermined minimum pressure value.

A further embodiment under the second aspect comprises selecting the band pass first filtering so that the energy difference in the filtered spectrum of the electric output signal between the maximum pressure applied and the minimum pressure applied becomes maximal.

Still a further embodiment under this second aspect comprises selecting band pass first filtering under the constraint that noise energy of the electric output signal, there where the filtering is effective, becomes at most equal to signal energy at the predetermined maximum pressure value.

Still in a further embodiment under this second aspect the upper cut-off frequency of the second filtering is selected below the transition frequency.

Still another embodiment under this second aspect comprises performing the second filtering there where the energy difference in the spectrum of the electric output signal of conversion is maximum between applying the maximum pressure value and the minimum pressure value which both establish for the pressure range to be monitored under this second aspect of the invention.

Under a third aspect the present invention provides for a method for monitoring pressure of a gas species which comprises
  exposing the gas species to transmission of laser light;
  periodically modulating the wavelength of the laser light over a wavelength band which includes at least one absorption line of the gas species;
  optoelectrically converting the transmitted laser light, thereby generating an electric output signal;
  inputting a signal which is dependent on the electric output signal of conversion to at least a first and a second parallel gas pressure monitoring channel;
  performing in the first channel first filtering and in the second channel second filtering;
  performing the first filtering so that the output signal thereof varies with a first characteristic as a function of pressure of said gas species;
  performing the second filtering so that the output signal thereof varies with a second characteristic as a function of the addressed gas pressure;
  further performing said first and second filtering so that the first characteristic becomes different from the second characteristic.
  From combining signals which are dependent on the output signals of the first and of the second filtering a pressure indicative signal is evaluated.

In an embodiment of this third aspect at least one of the first and of the second filtering is performed as band pass filtering.

In an embodiment under this third aspect first and second filtering is performed in non-overlapping frequency areas of the spectrum of the electric output signal.

In a further embodiment under this third aspect the first and the second filtering are performed as band pass filtering.

In a further embodiment under the third aspect of the present invention the first and second filtering are performed in respective first and second frequency ranges, whereby the energy of the electric output signal has a first energy vs. pressure characteristic in the first frequency range and has a second energy vs. pressure characteristic in the second frequency range, whereby the first and second energy characteristics are different from each others.

In a further embodiment which is applicable to the present invention under all its aspects there is prestored a first reference characteristic which represents the first characteristic and/or there is prestored a second reference characteristic which represents the second characteristic. The addressed characteristics are the characteristics with which the output signal of the respective filtering varies as a function of pressure of the gas species to be monitored.

Then momentary signals which depend from signals of the first and/or second filterings respectively are compared with a stored first and second reference characteristic, whereby first and second pressure indicative signals are generated. Thus, momentarily prevailing filtering results become compared with predetermined signal vs. pressure characteristics to establish from the prevailing signals to which pressure value they accord.

Still in another embodiment under the third aspect of the present invention, but also applicable to the invention under the first and second aspects, the first filtering generates a first output signal which has first derivatives vs. pressure within a predetermined pressure range. The second filtering generates a second output signal which has second derivatives vs. pressure in the addressed predetermined pressure range. Thereby, absolute values of one of the addressed first and second derivatives are smaller than absolute values of the other of the addressed derivatives in at least one common subpressure range of the predetermined pressure range. Thereby, when speaking of signal derivatives we clearly disregard signal noise which makes derivative values random.

In a further embodiment under the third aspect but also applicable to the invention under the first and second aspects the second filtering generates a second output signal which has exclusively positive or negative derivatives vs. pressure in a predetermined pressure range. The first filtering generates a first output signal with first derivatives vs. pressure which are exclusively positive in at least one pressure subrange of the predetermined pressure range and which are exclusively negative in at least one second subrange of the addressed predetermined pressure range. Thereby, the absolute values of the second derivatives are smaller in at least one of the addressed pressure subranges than the absolute values of the first derivatives also considered in the addressed at least one of the subranges and again without considering noise.

In an embodiment especially under the third aspect of the present invention from a signal dependent on the second output signal of second filtering one of the pressure subranges is determined.

In a further embodiment from this pressure subrange determined and from the first output signal, i.e. of first filtering, a pressure indicative signal is determined.

Under the third aspect of the present invention a further embodiment comprises
  predetermining a maximum pressure to be monitored;
  performing at least one of the following steps, namely
    performing the second filtering with a band pass filter characteristic which has an upper cut-off frequency not higher than a transition frequency and which has a lower cut-off frequency which is above modulation frequency of periodic wavelength modulation and performing first filtering with a filter characteristic which has a lower cut-off frequency which is not lower than the transition frequency.

Thereby, the addressed transition frequency is determined in the spectrum of the electric output signal there where the caustic function of the pressure-dependent spectrum envelopes of the electric output signal touches the envelope of the spectrum at the maximum pressure.

Thereby, in one embodiment first as well as second filtering are performed.

Thereby, in a further embodiment first filtering is performed as band pass filtering.

Thereby, in a further embodiment first filtering is performed with a lower cut-off frequency higher than the transition frequency.

Thereby, in another embodiment first filtering is performed as a band pass filtering and there is determined a filter frequency which is above the lower cut-off frequency of first filtering there where the derivative of spectral amplitude vs. pressure of the electric output signal of conversion at least approximately accords with the desired characteristic. Then band pass first filtering is performed with the determined filter frequency as band pass center frequency.

Thereby, another embodiment comprises performing the first filtering as band pass filtering, thereby selecting bandwidth of band pass first filtering with the target of achieving a desired signal to noise ratio.

Thereby, a further embodiment comprises selecting an upper cut-off frequency of the second filtering below the transition frequency.

Thereby, a further embodiment comprises performing the second filtering with a center frequency there where the derivative of spectral amplitude vs. pressure of the electric output signal at least approximately accords with a desired characteristic.

Thereby, still a further embodiment comprises performing the second filtering with a bandwidth for a desired signal to noise ratio.

Thereby, an embodiment further comprises performing the second filtering and realizing a desired sensitivity of the output signal of the second filtering under consideration of noise by performing the following steps subsequently once or repeatedly in one or more than one loops:

a) Determining a center frequency of the second filtering there where the derivative of spectral amplitude vs. pressure of the electric output signal at least approximately accords with a desired characteristic and b) tailoring bandwidth of the second filtering for a desired signal to noise ratio.

Still under the third aspect one embodiment comprises performing monitoring in a predetermined pressure range between a minimum pressure value and a maximum pressure value;

performing at least one of the following steps:

second filtering with a band pass filter characteristic which has an upper cut-off frequency not higher than a transition frequency and which has a lower cut-off frequency which is above modulation frequency of the periodic wavelength modulation;

first filtering with a filter characteristic which has a lower cut-off frequency not lower than the transition frequency;

whereby the transition frequency is determined in the spectrum of the electric output signal there where the spectrum envelopes of the electric output signal at said minimum pressure value and at said maximum pressure value intersect.

Thereby, a further embodiment comprises performing both first and second filterings. Still a further embodiment comprises performing the first filtering as a band pass filtering.

Thereby, a further embodiment comprises performing the first filtering with a lower cut-off frequency which is higher than the just addressed transition frequency. Thereby, in another embodiment first filtering is performed between the transition frequency and a noise limit frequency. The noise limit frequency is defined there where noise energy of the electric output signal equals signal energy of the electric output signal at the addressed minimum pressure value.

Thereby, in a further embodiment band pass first filtering is selected so that the energy difference in the filtered spectrum of the electric output signal between applying the maximum pressure value and the minimum pressure value becomes maximum.

Thereby, still a further embodiment comprises selecting the band pass first filtering under the constraint that noise energy of the electric output signal there where the first filtering is effective is at most equal to signal energy at the maximum pressure as predetermined.

Thereby, in a further embodiment the upper cut-off frequency of the second filtering is selected below the transition frequency as addressed.

Still further, in an embodiment second filtering is performed there where the energy difference in the spectrum of the electric output signal of conversion is maximum between applying the maximum predetermined pressure value and the minimum predetermined pressure value.

Still in a further embodiment under all three aspects of the present invention the gas species monitored is oxygen.

Still in a further embodiment under all three aspects of the present invention there is generated a reference pressure indicative signal by performing the monitoring according to the present invention at a predetermined pressure of the gas species.

Yet under a further embodiment there is generated a resulting pressure indicative signal in dependency of a difference of the reference pressure indicative signal and the pressure indicative signal.

Still a further embodiment under all the aspects of the present invention comprises monitoring transmission of the laser light along a trajectory path to which the gas species is or is to be applied and thereby generating a transmission indicative signal. Signals from which the pressure indicative signal depends are then weighted in dependency of the transmission indicative signal.

Still a further embodiment of the invention under all its aspects further comprises providing a gas with the gas species in at least one container which is transparent for the addressed laser light.

Thereby, in a further embodiment such container is provided and monitored in ambient air.

Still in a further embodiment monitoring transparency of the trajectory path for the laser light includes the addressed transparent container, whereby a transparency indicative signal is generated. Signals wherefrom the pressure indicative signal depends are then weighted in dependency of the transmission indicative signal.

Thereby, in a further embodiment there is provided a third parallel channel as a calibration channel and there is generated the addressed transmission indicative signal in the said calibration channel.

In a further embodiment a reference signal is generated by performing the monitoring according to the present invention at a reference container with a predetermined amount of the gas species, whereby a result pressure indicative signal is generated in dependency of the difference from said reference signal and the pressure indicative signal.

Still a further embodiment comprises checking the pressure indicative signal on plausibility.

Still a further embodiment comprises monitoring oxygen pressure in the addressed containers.

Still a further embodiment comprises that the addressed containers are filled with a product.

Still in a further embodiment the addressed containers are substantially of glass or plastic material. Thereby, still in a further embodiment such containers are vials.

Still in a further embodiment a container, whereat the gaseous content is monitored, is one of a multitude of containers which are conveyed in a stream towards, past and from the addressed monitoring.

Still in a further embodiment the container being monitored and the laser light transmitted therethrough are moved in synchronism during monitoring.

Still a further embodiment comprises monitoring subsequently the gas pressure in a multitude of containers which are conveyed subsequently towards, past and from the monitoring, thereby generating a reference pressure indicative signal by applying to the monitoring at least one reference container with a predetermined amount of the gas species to be monitored before monitoring one of the multitude of containers. There is thereby generated a result pressure indicative signal in dependency of the reference pressure indicative signal and the pressure indicative signal.

Further, in an embodiment the reference pressure indicative signal is generated each time just before monitoring one of the multitude of containers.

Still in a further embodiment reference pressure indicative signals from subsequent monitoring of reference containers with the predetermined amount of gas species are averaged and the addressed difference is formed in dependency of the result of such averaging.

The present invention is further directed on a method for manufacturing closed, possibly filled containers which are transparent to laser light and with a predetermined maximum amount of oxygen, which manufacturing method comprises the steps of manufacturing closed, possibly filled and transparent containers and subjecting these containers to a gas pressure monitoring as was disclosed above and according to one of the different aspects and embodiments of the present invention and rejecting containers if a signal which depends from the pressure indicative signal is indicative for an oxygen pressure in such container above a predetermined maximum value.

There is further proposed according to the present invention an apparatus for performing the present invention under all its method aspects.

With an eye especially on monitoring oxygen pressure the following dimensioning rules may be followed:

Center frequency of second filtering band pass, $f_{ZII}$, relative to laser wavelength modulation frequency $f_C$:

$$10 \leq f_{ZII}/f_C \leq 20$$

Center frequency of band pass applied for first filtering, $f_{ZI}$ relative to modulation frequency $f_C$:

$$50 \leq f_{ZI}/f_C \leq 120$$

Pass bandwidth of second filtering relative to modulation frequency:

$$1 \leq B_{II}/f_C \leq 18$$

Pass bandwidth of band pass first filtering, $B_I$, relative to modulation frequency $f_C$:

$$50 \leq B_I/f_C \leq 1000$$

Deviation H of wavelength modulation of the laser:

At least 5 pm, thereby preferably 50 pm $\leq H \leq 500$ pm.

Further, one laser which may be applied in context with the present invention is the Vertical Cavity Surface Emitting laser.

Figure 2:
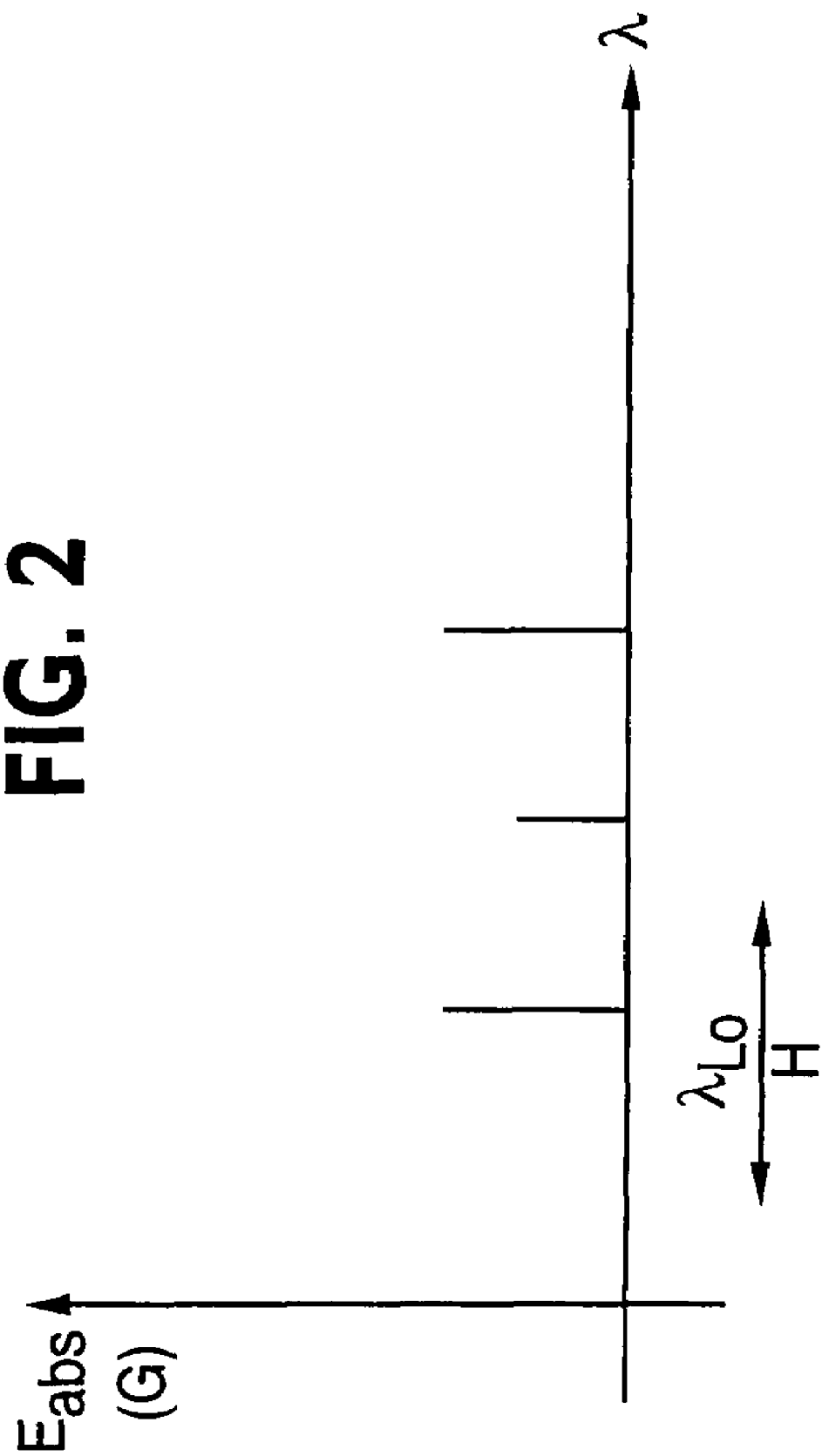
Figure 3:
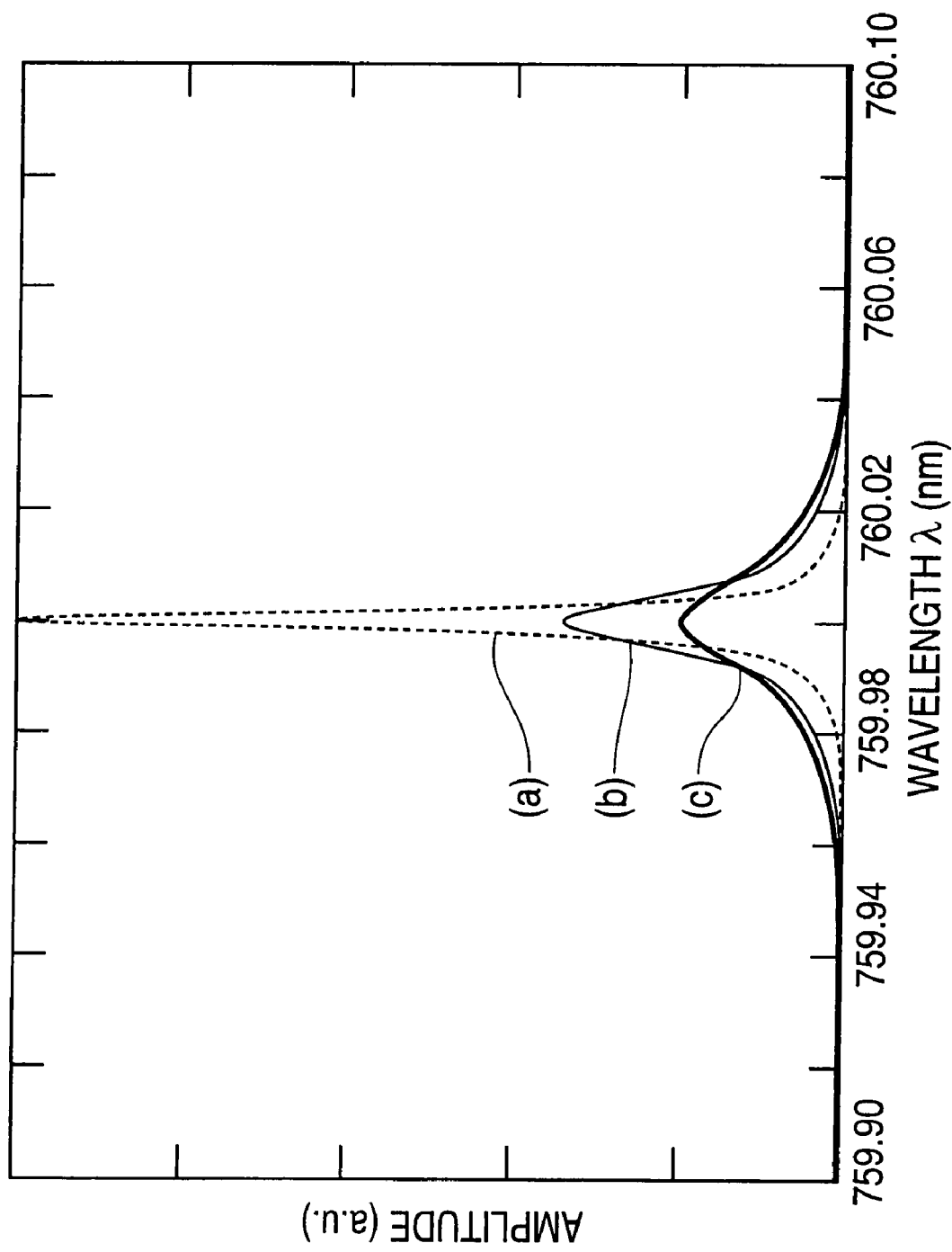
Figure 4:
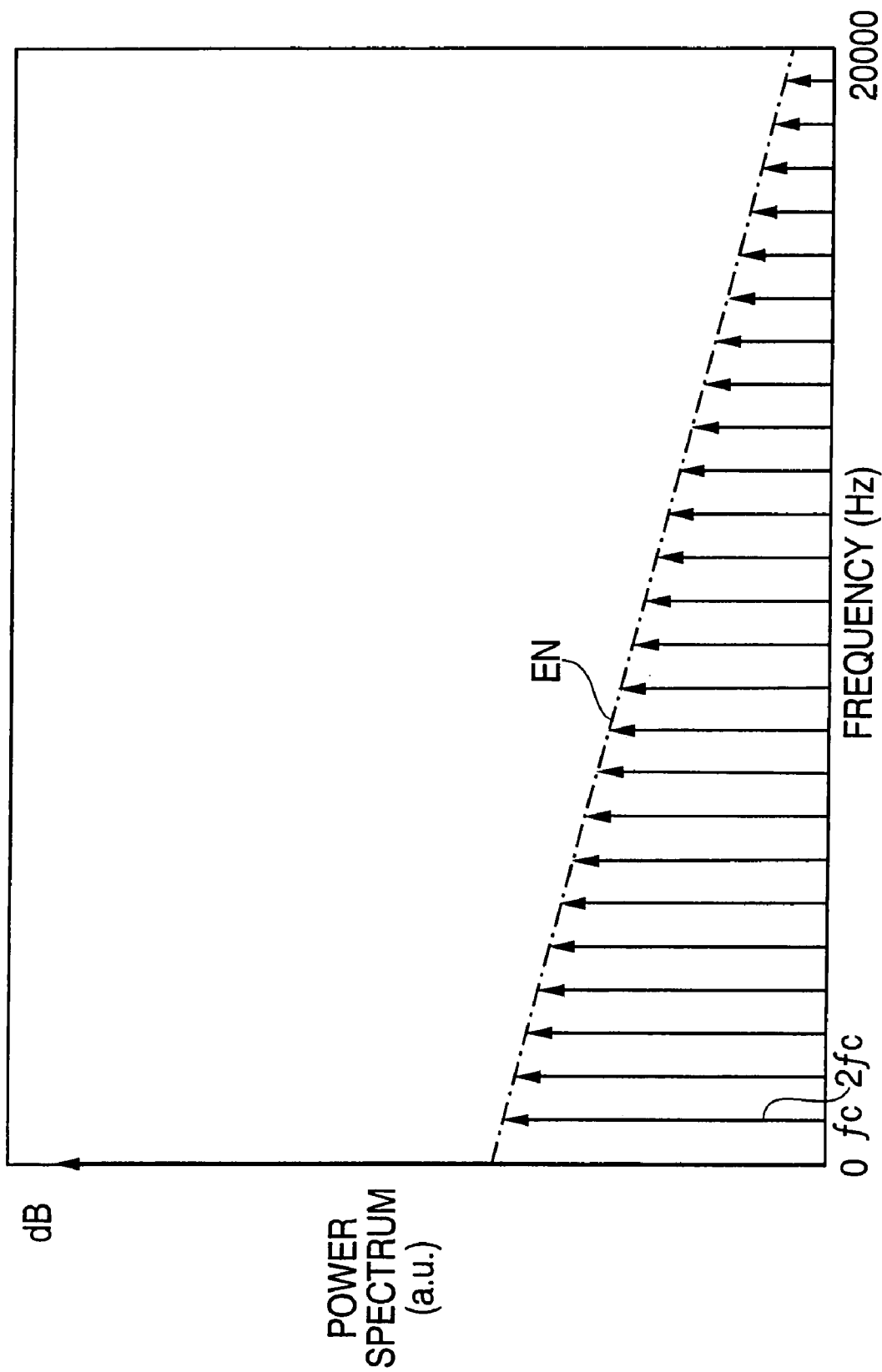
Figure 5:
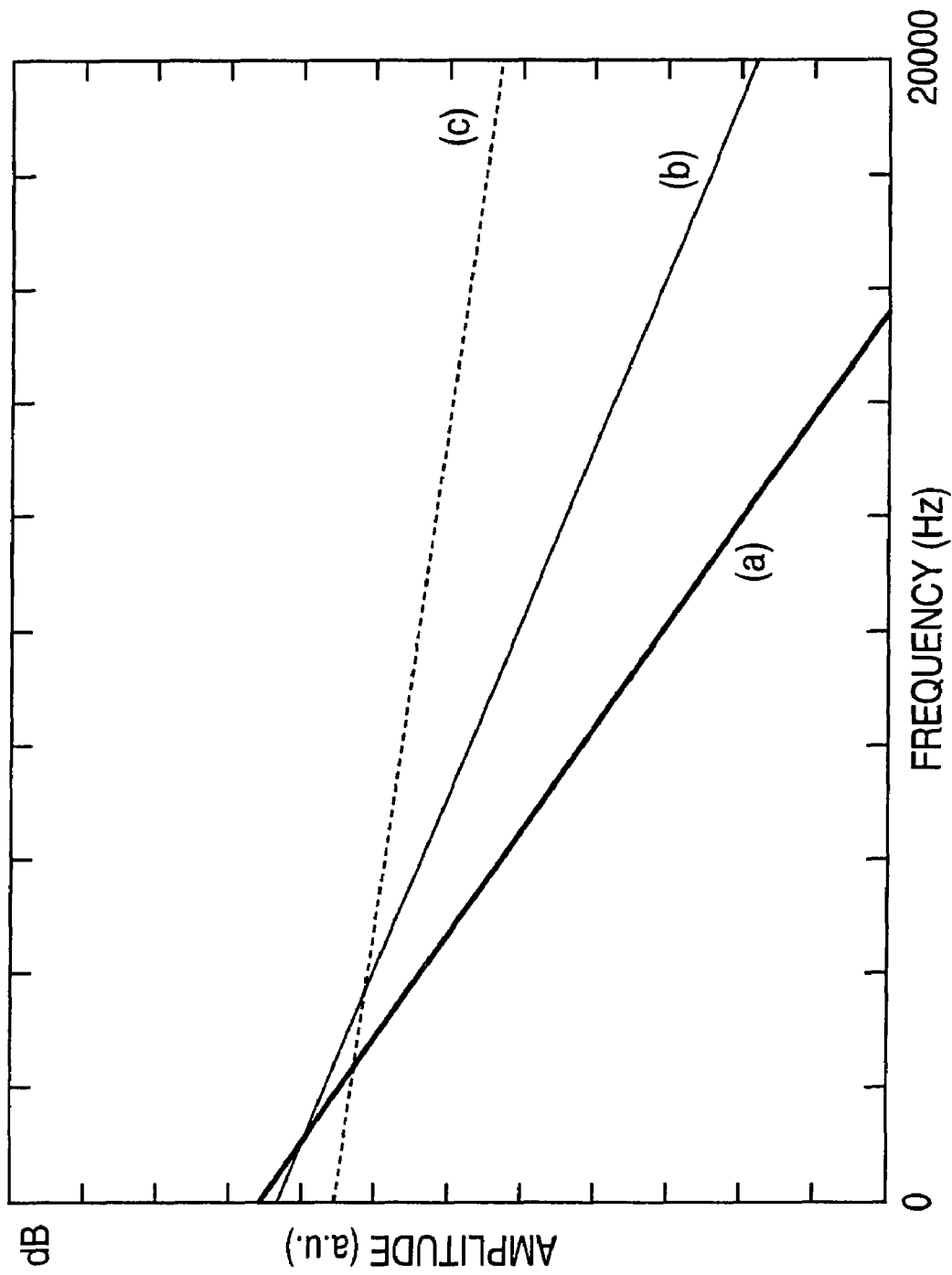
Figure 6:
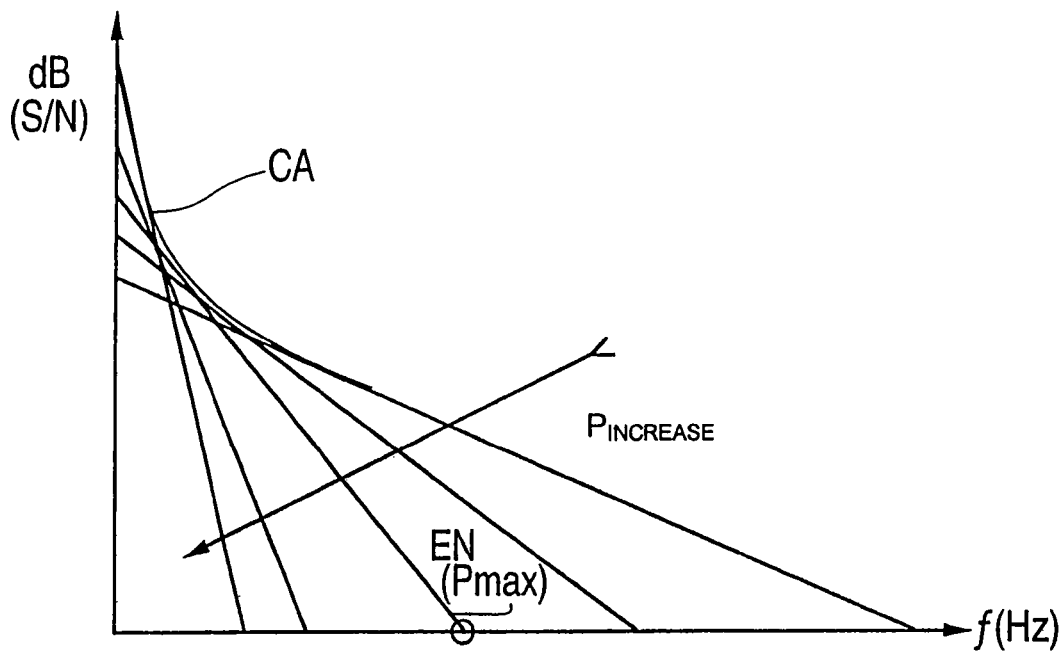
Figure 7:
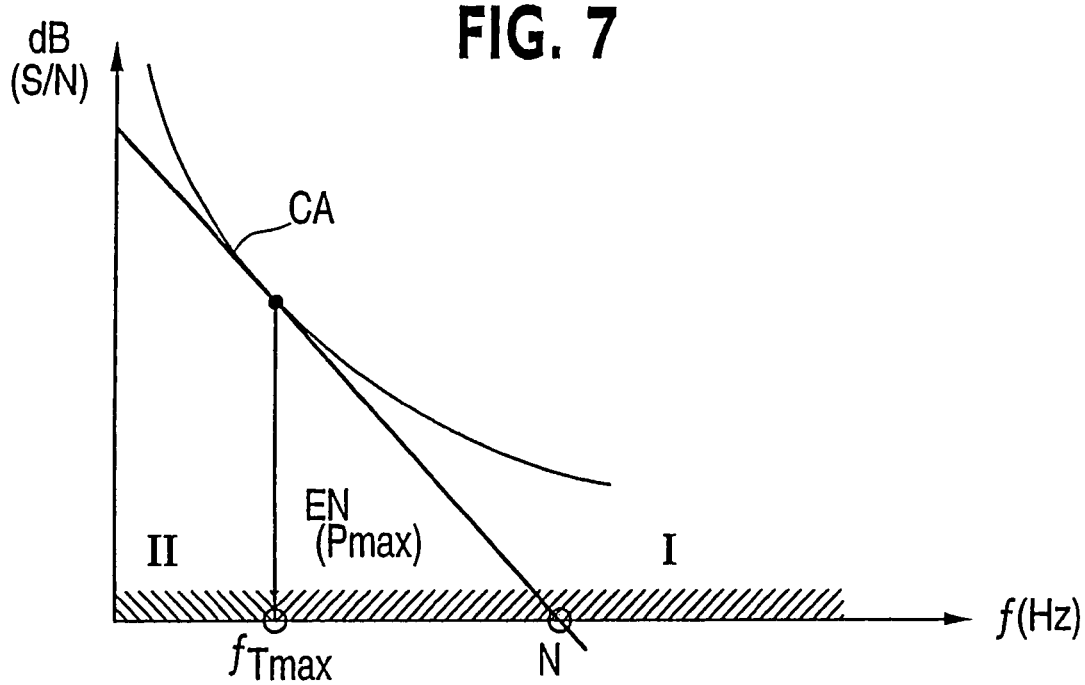
Figure 8:
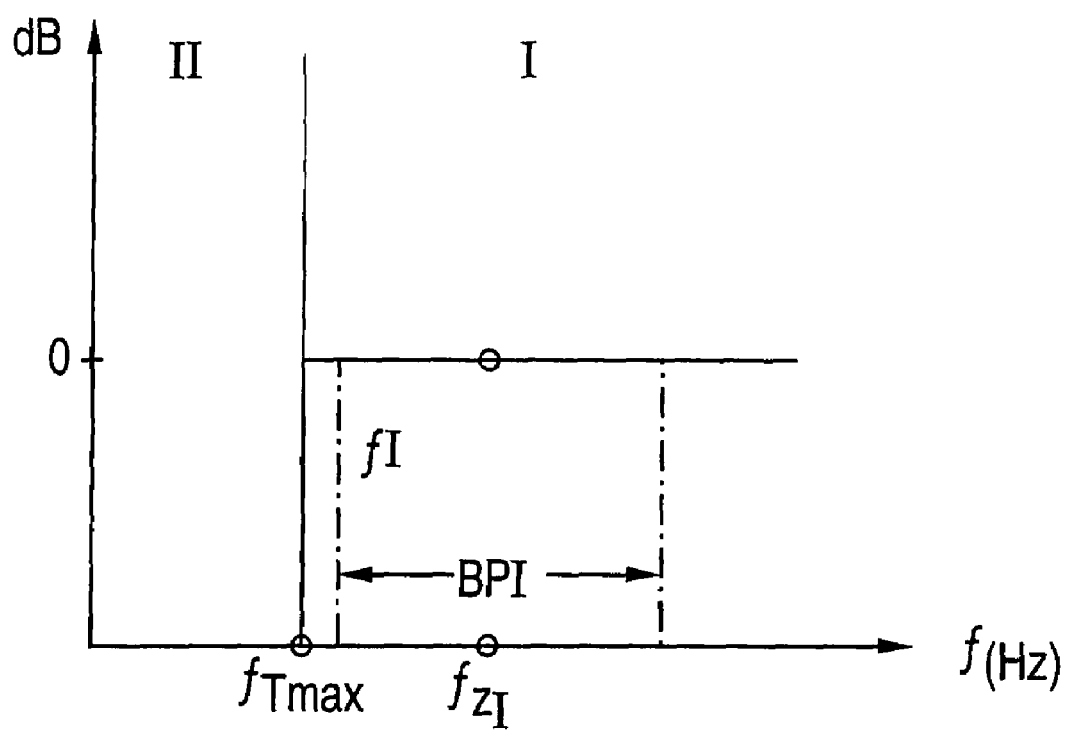
Figure 9:
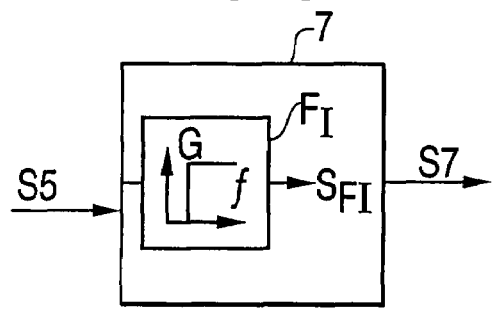
Figure 10:
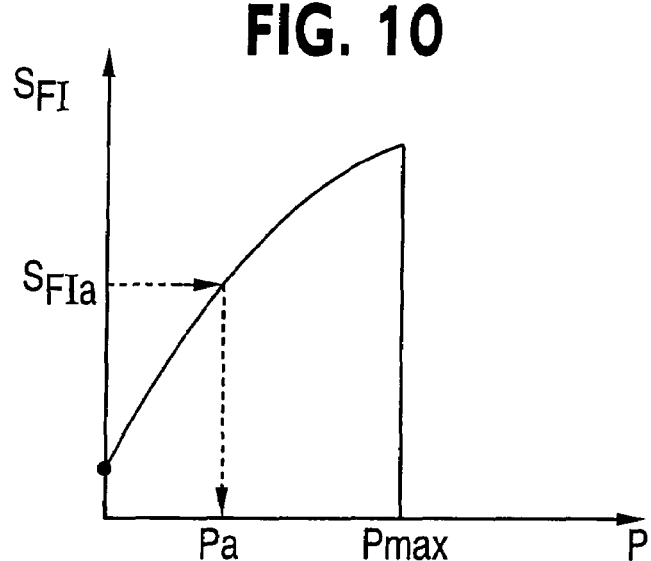
Figure 11:
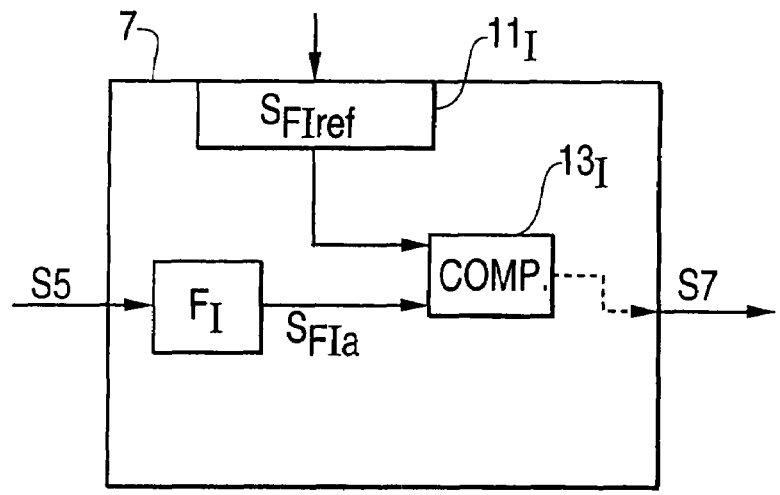
Figure 12:
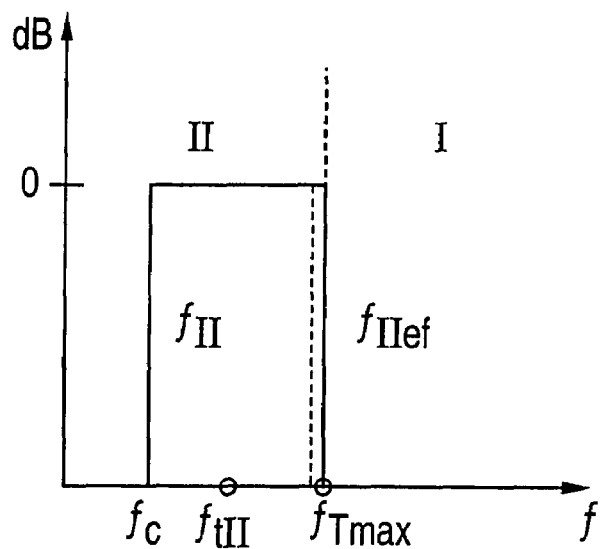
Figure 13:
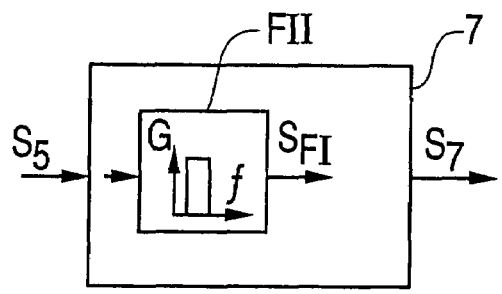
Figure 14:
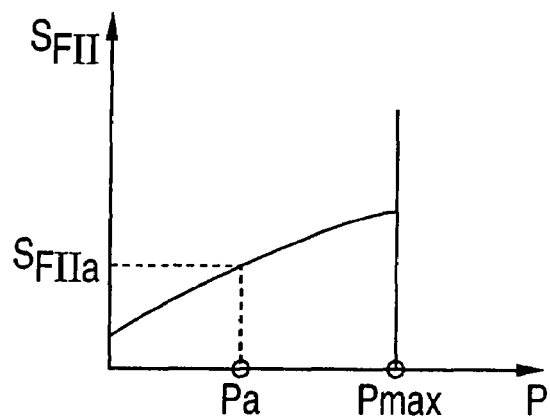
Figure 15:
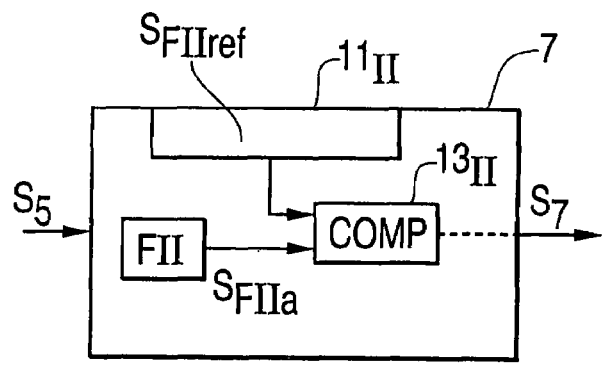
Figure 16:
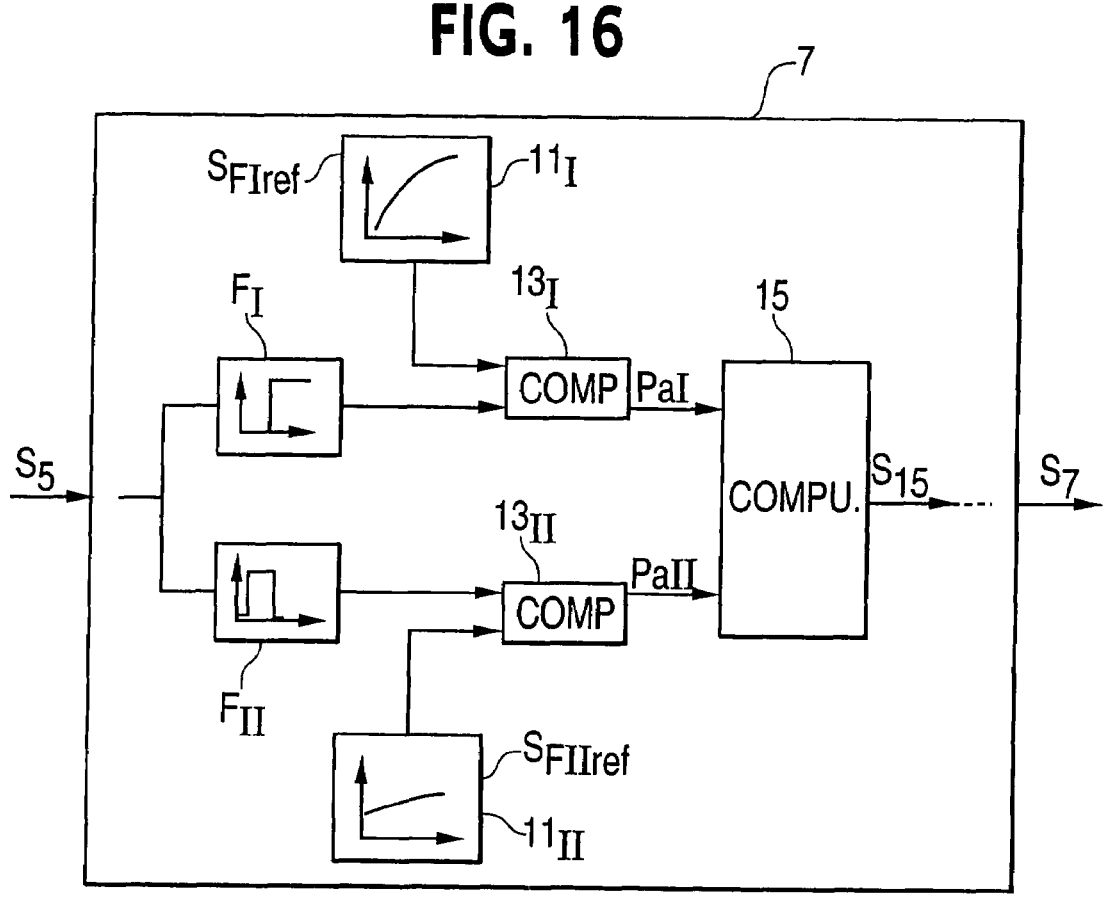
Figure 17:
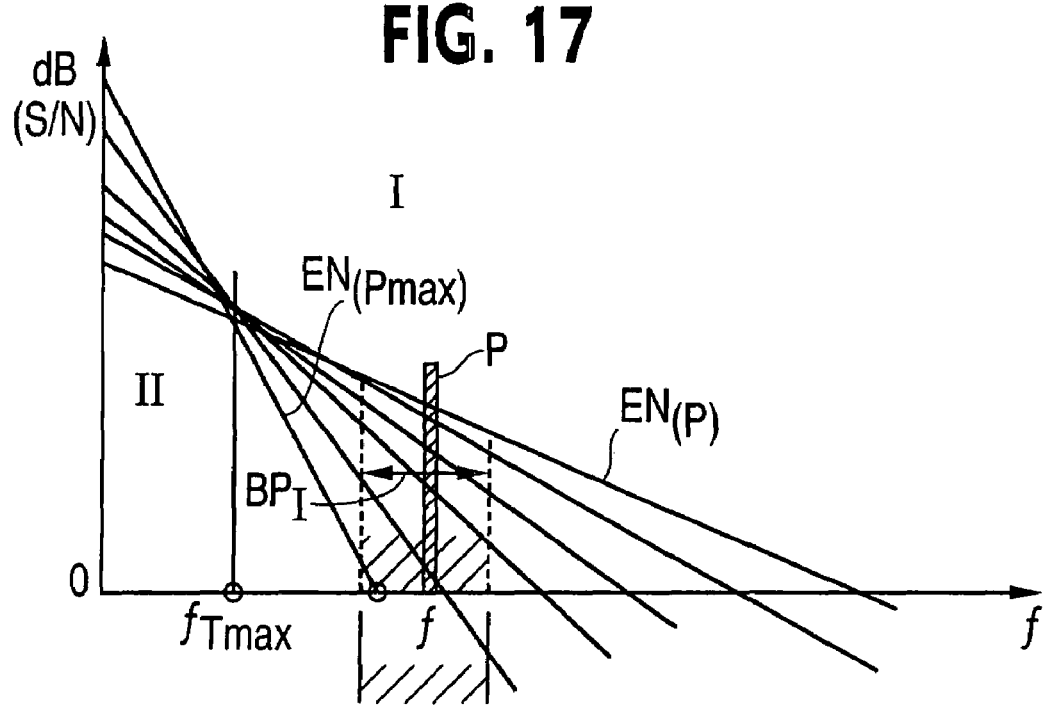
Figure 18:
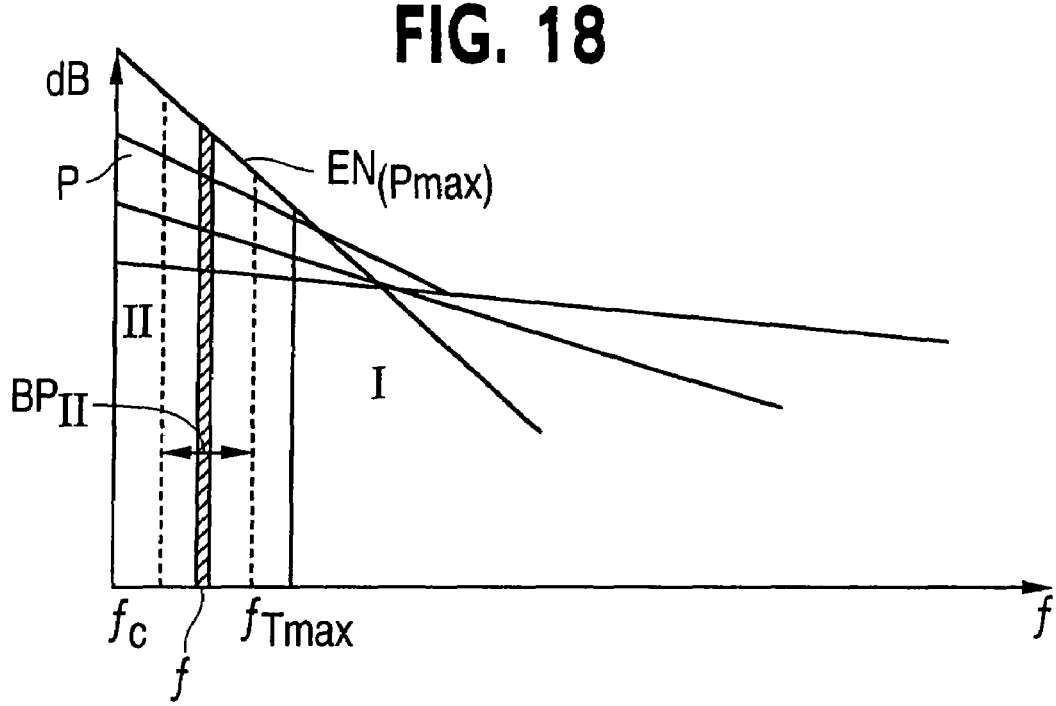
Figure 19:
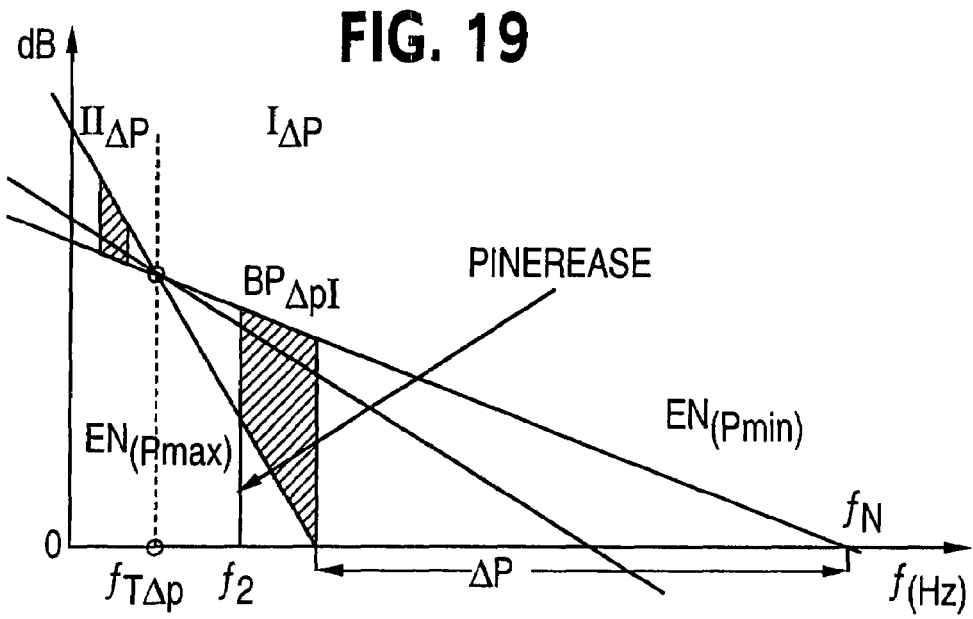
Figure 20:
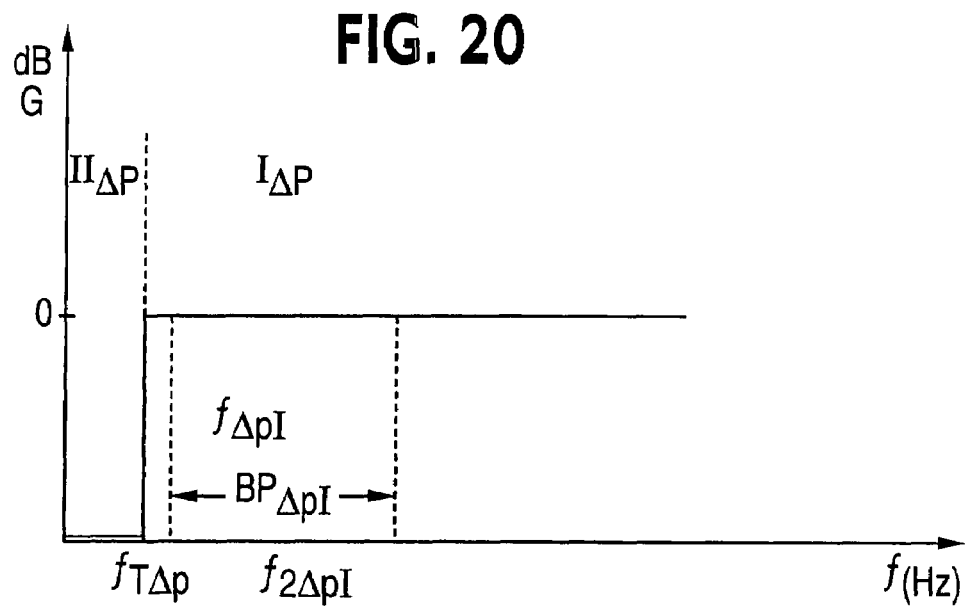
Figure 21:
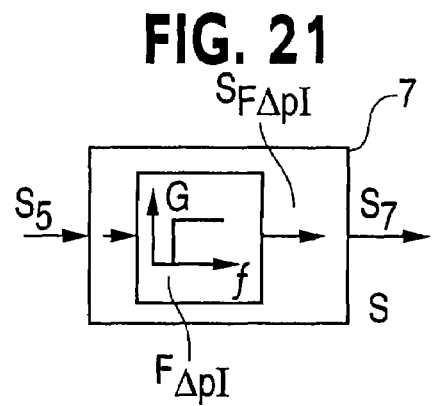
Figure 22:
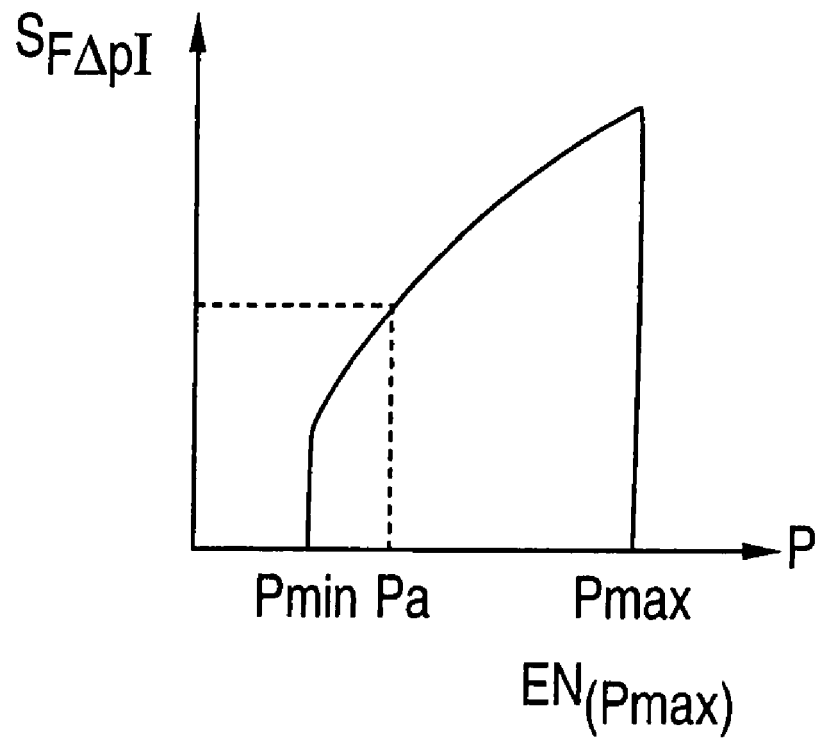
Figure 23:
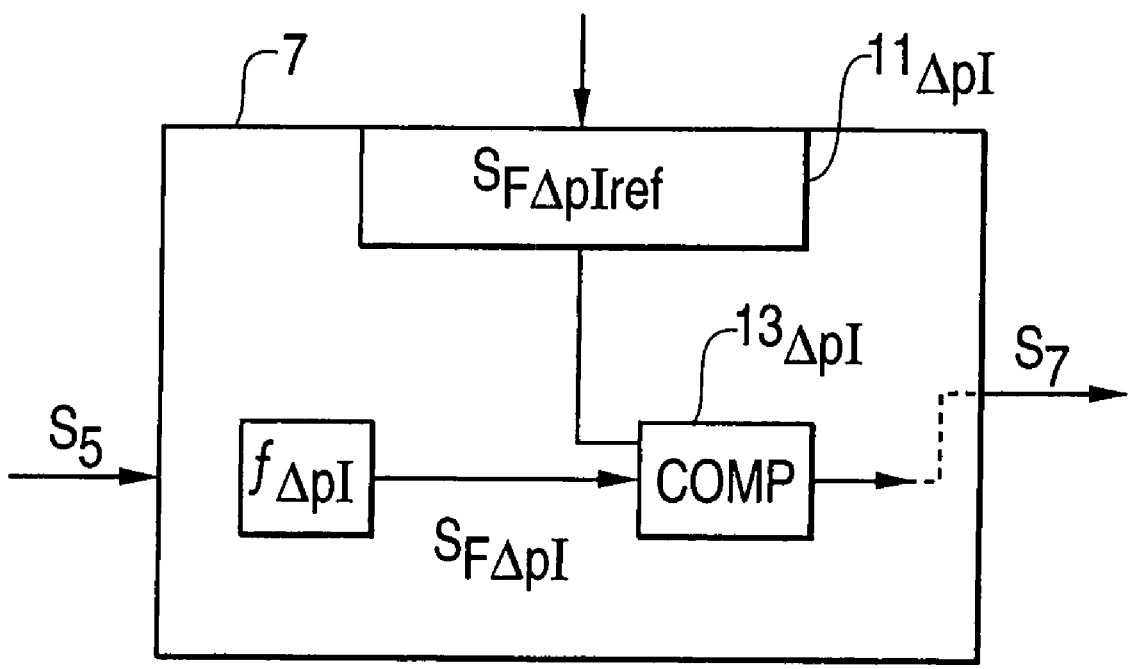
Figure 24:
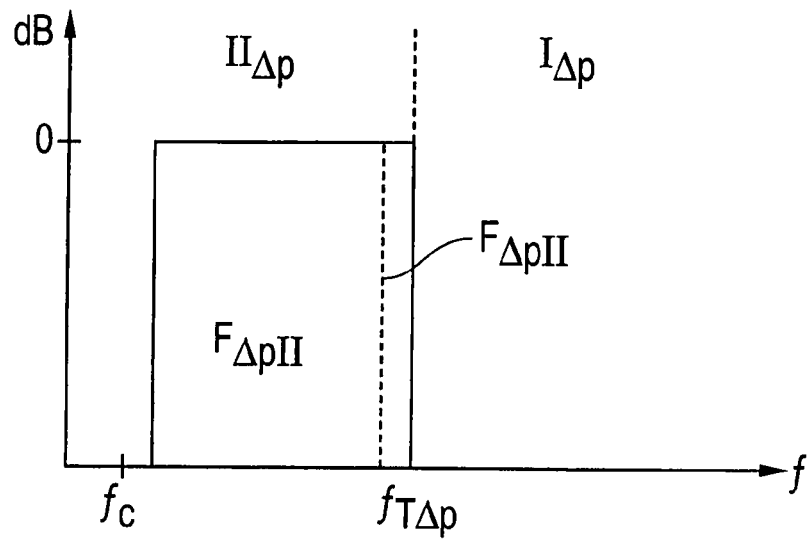
Figure 25:
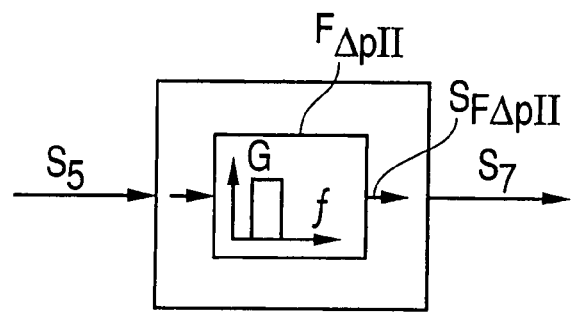
Figure 26:
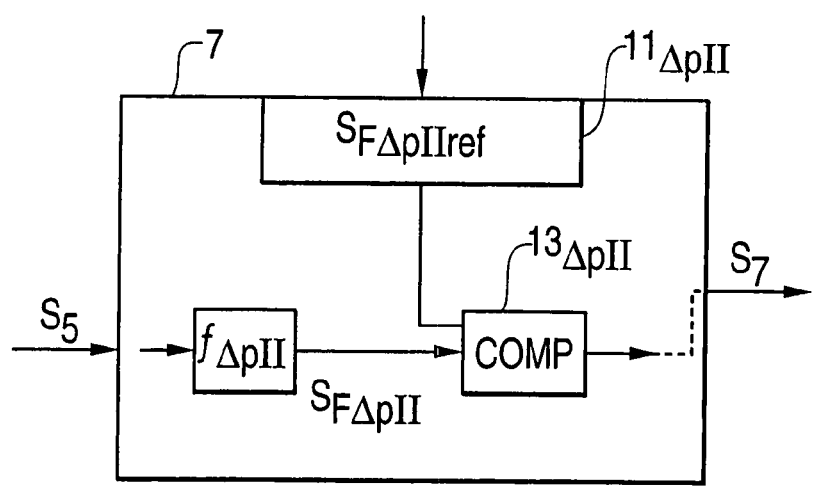
Figure 27:
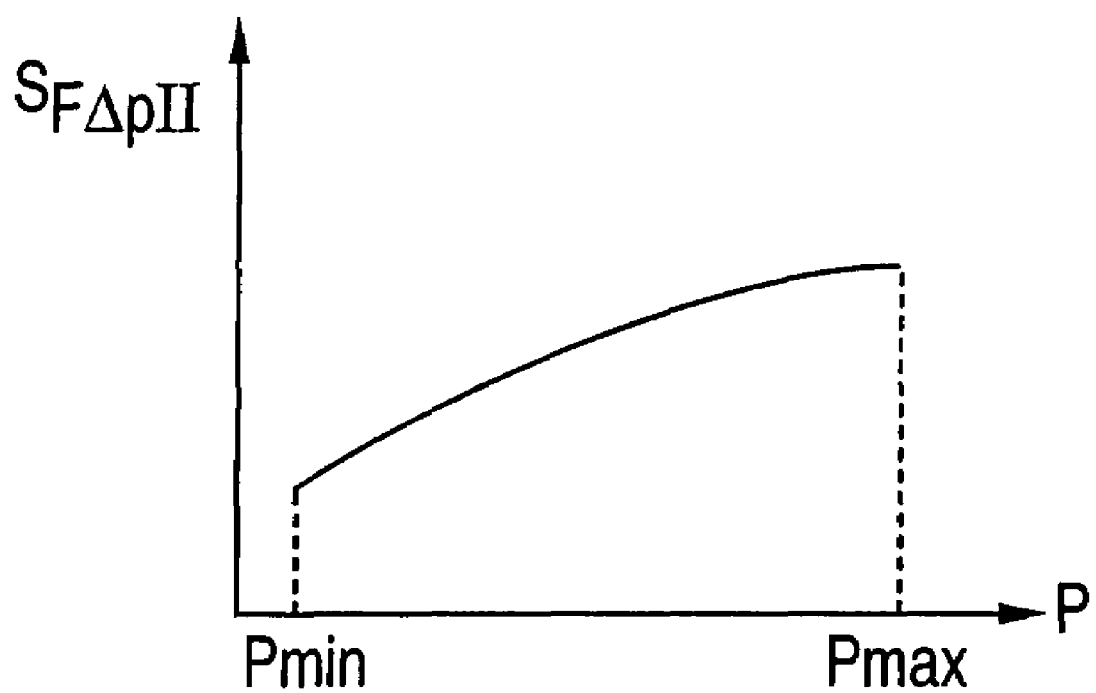
Figure 28:
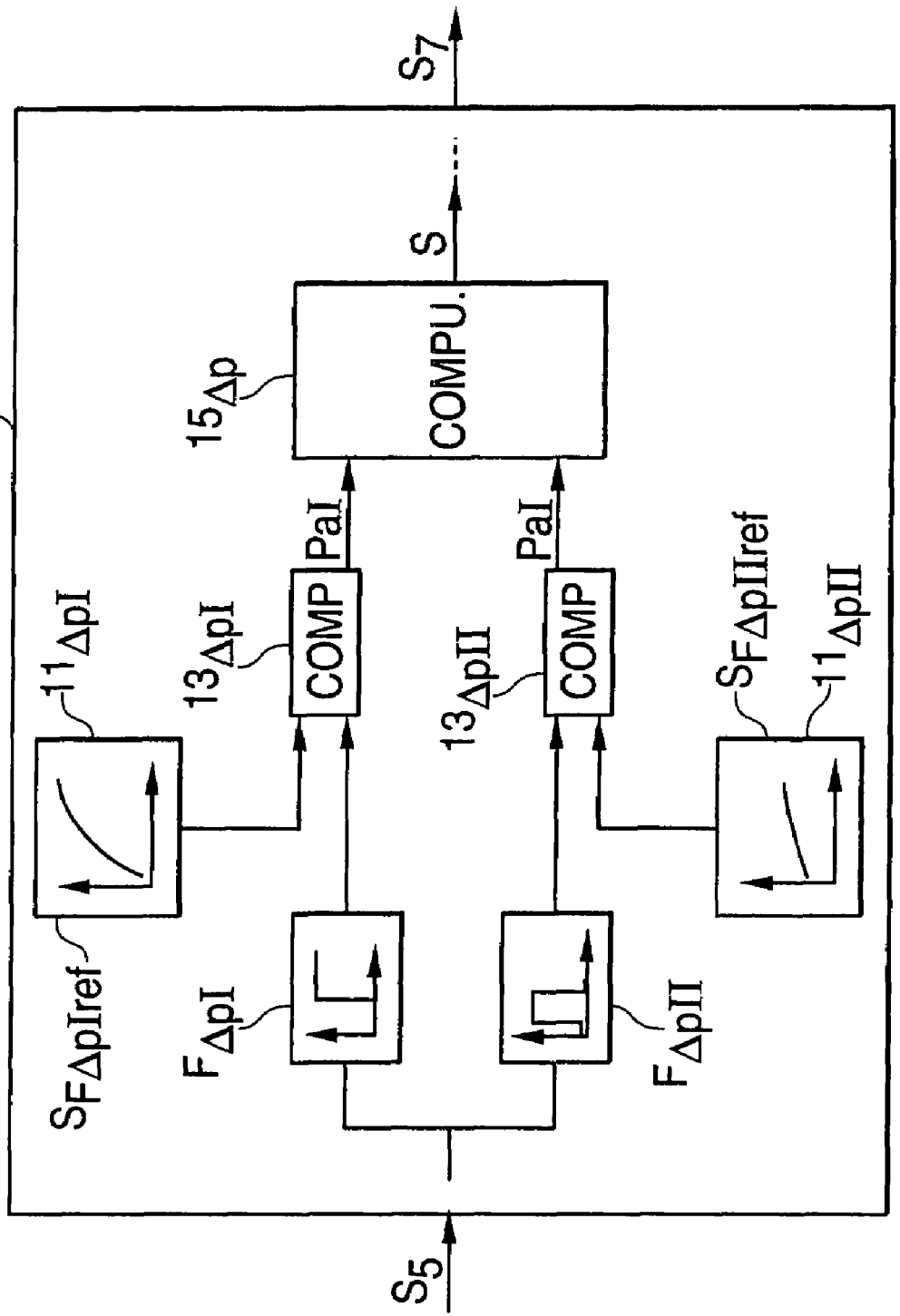
Figure 29:
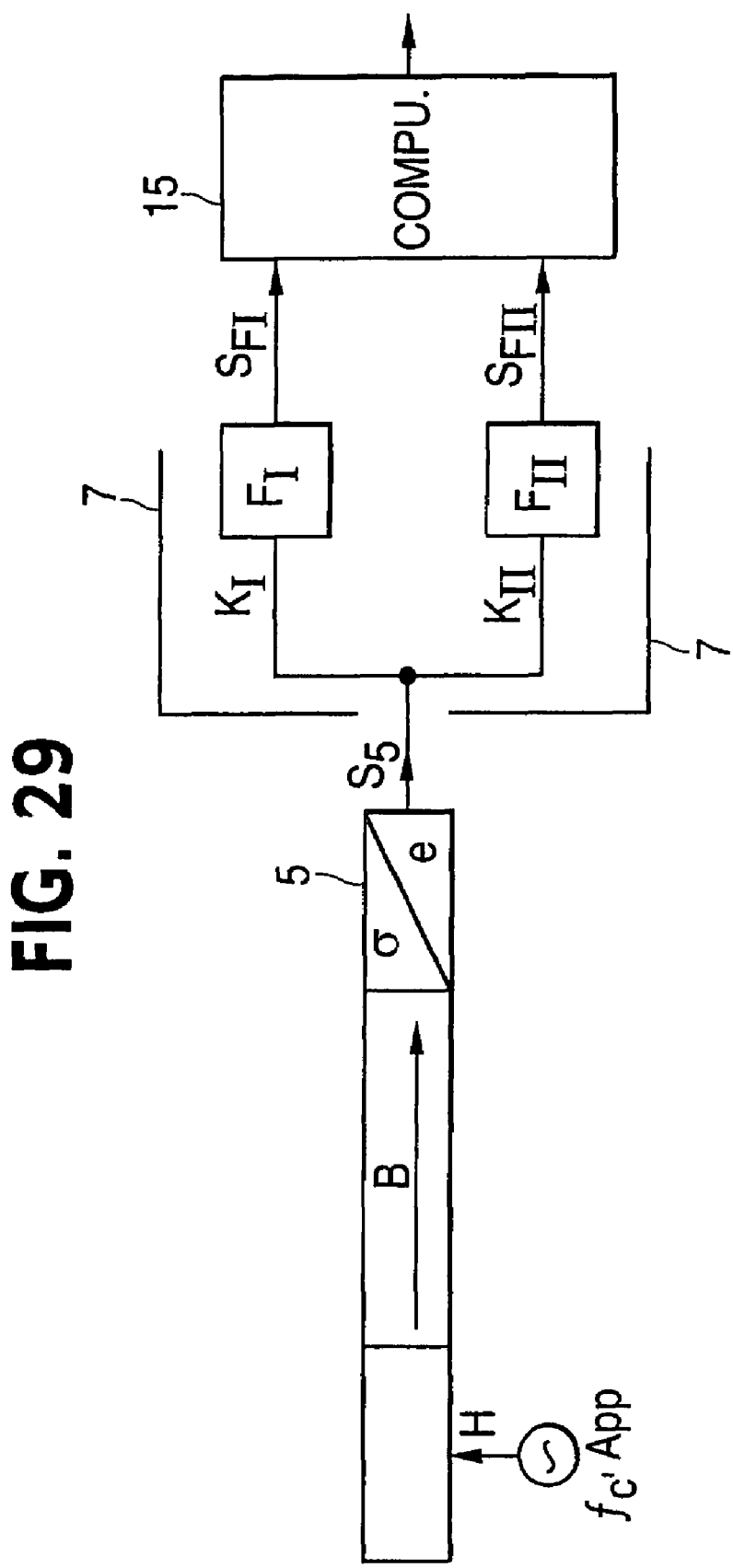
Figure 30:
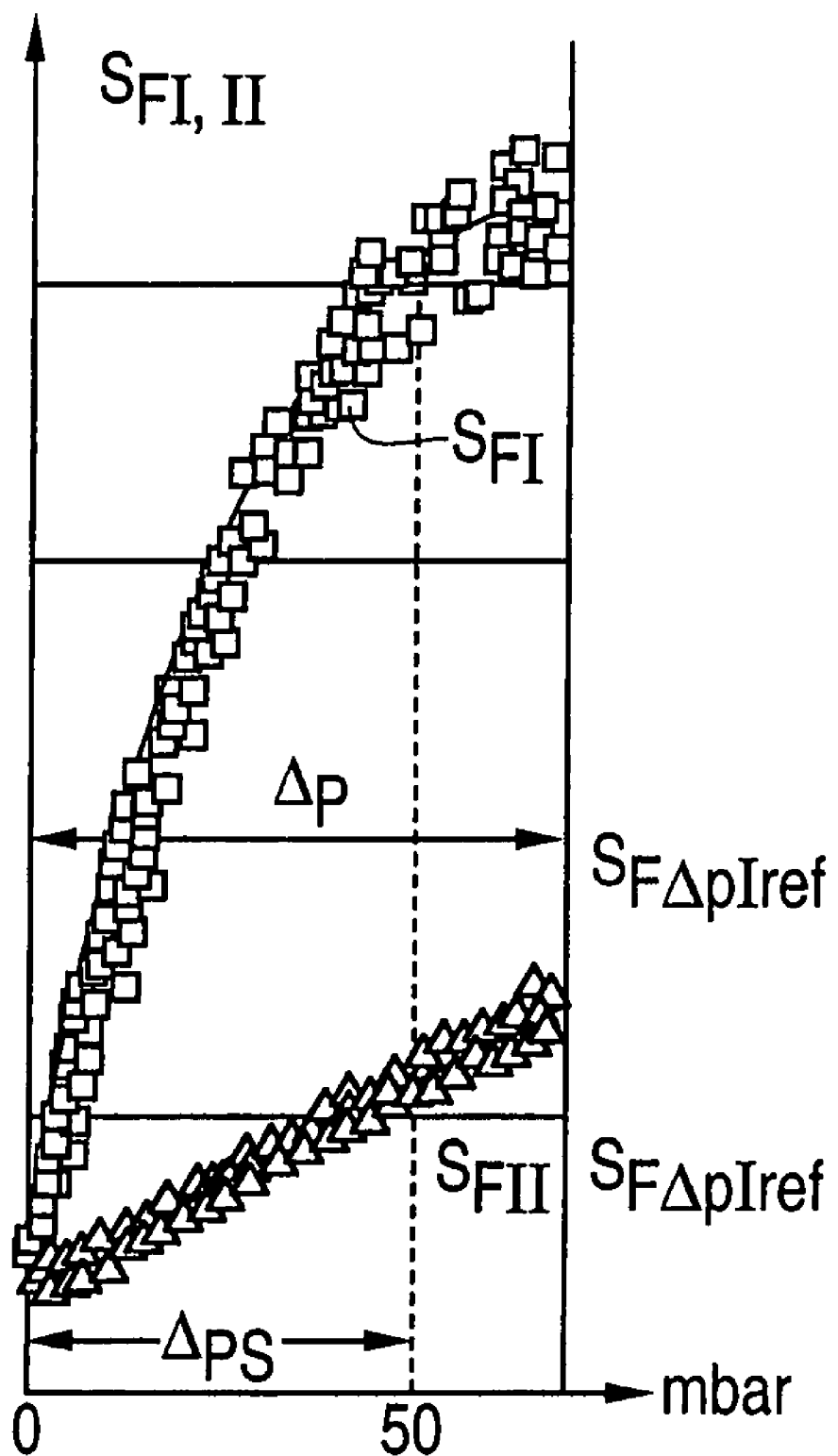
Figure 31:
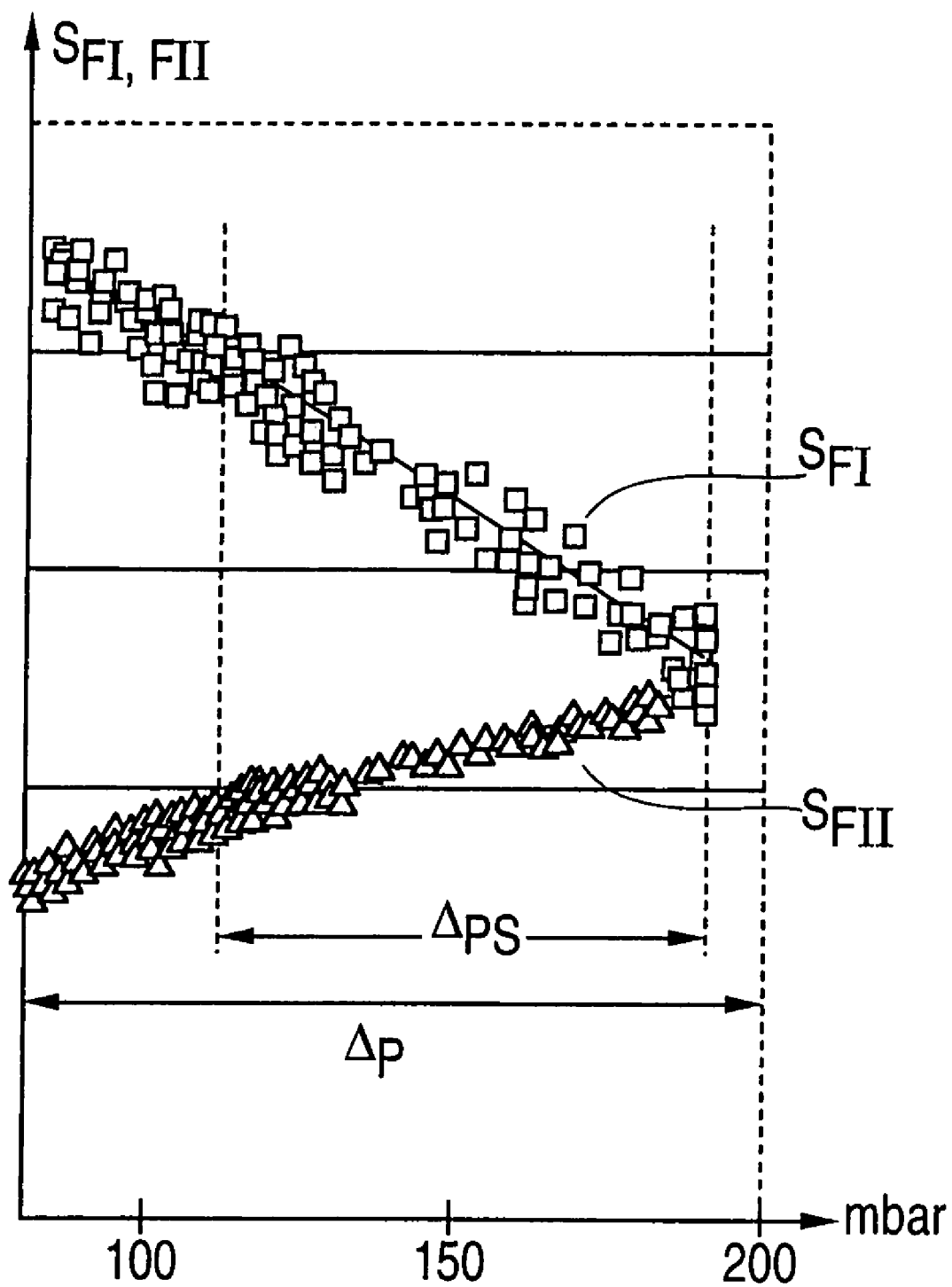
Figure 32:
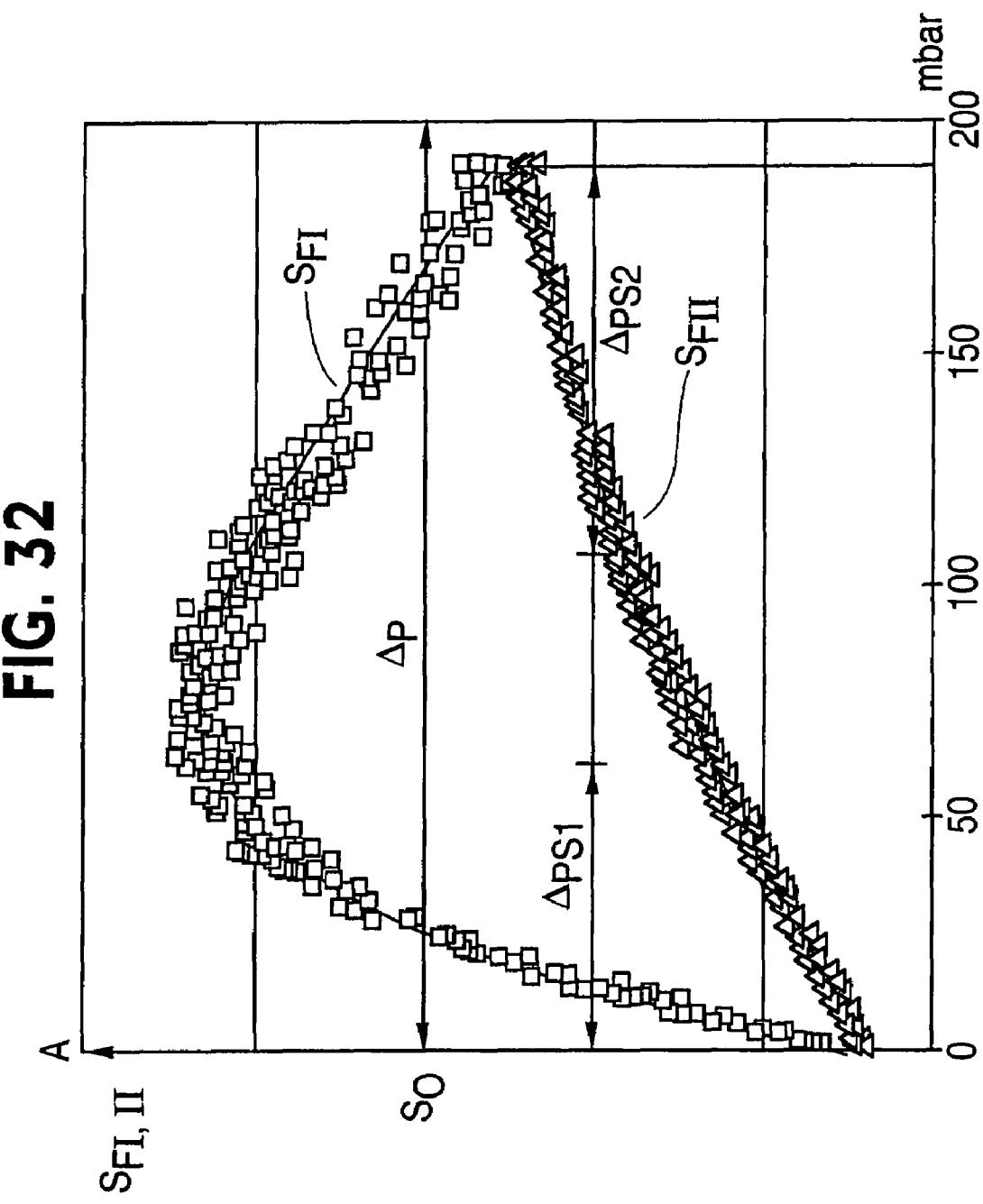
Figure 33:
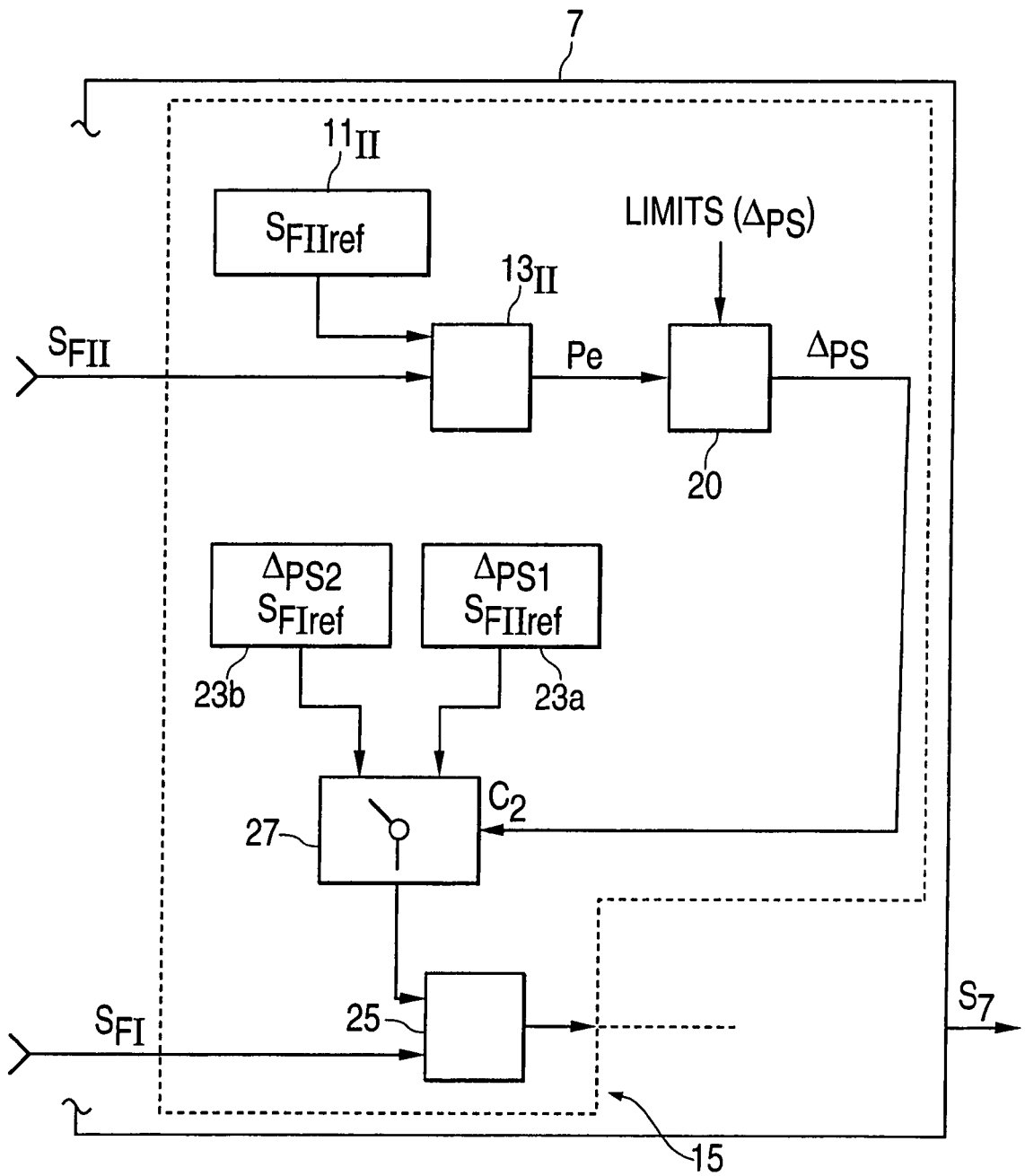
Figure 34:
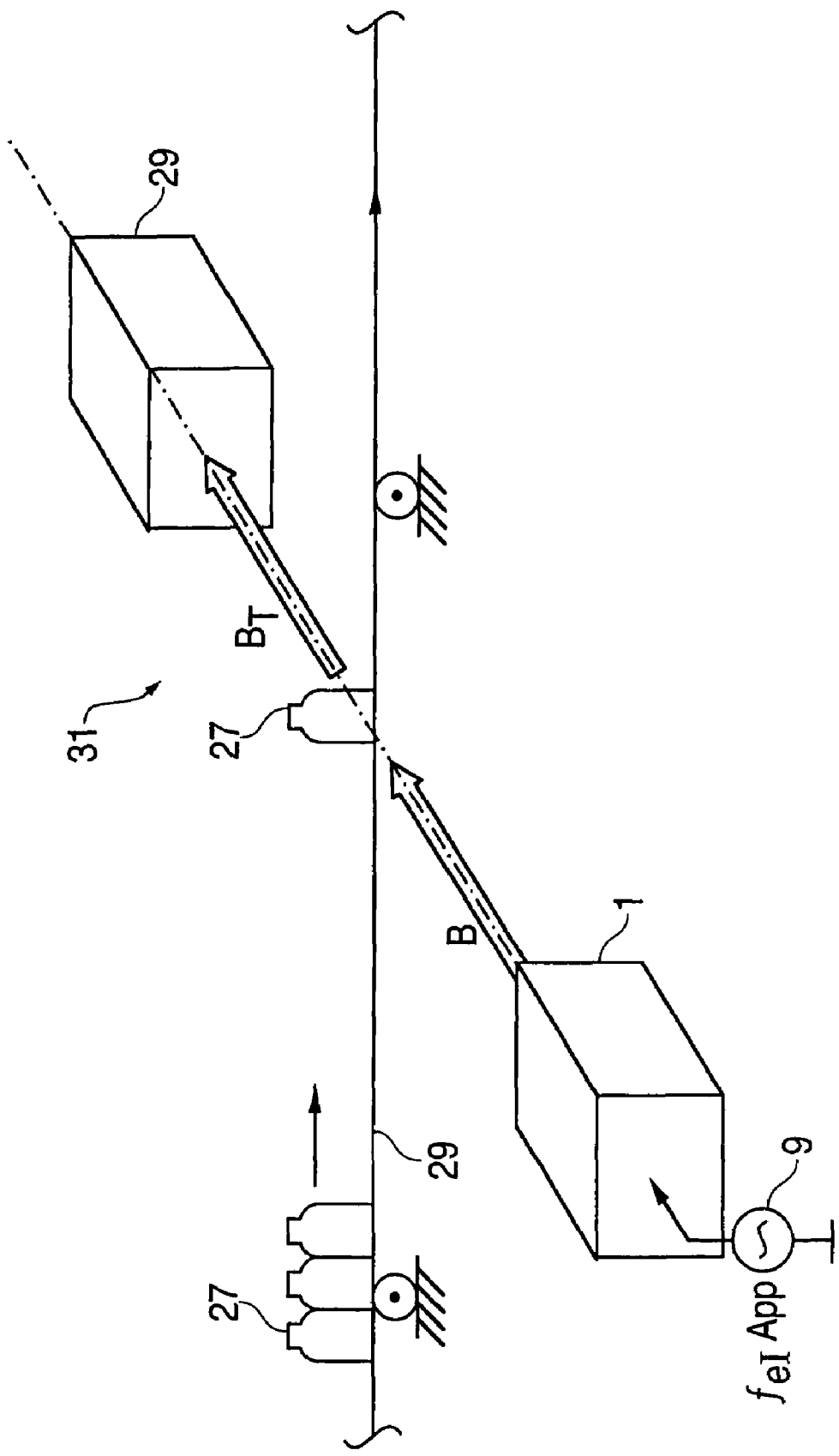
Figure 35:
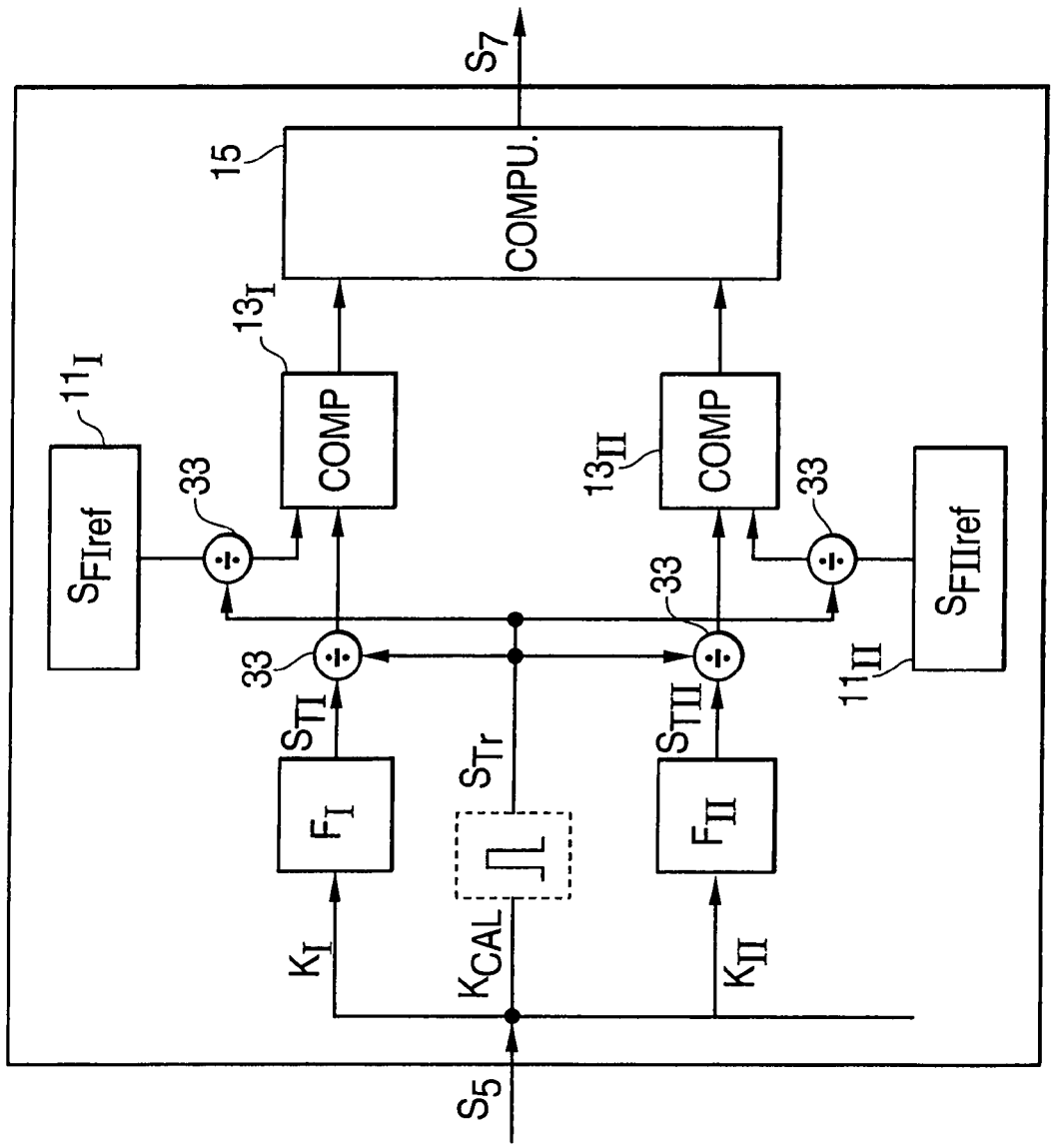
Figure 36:
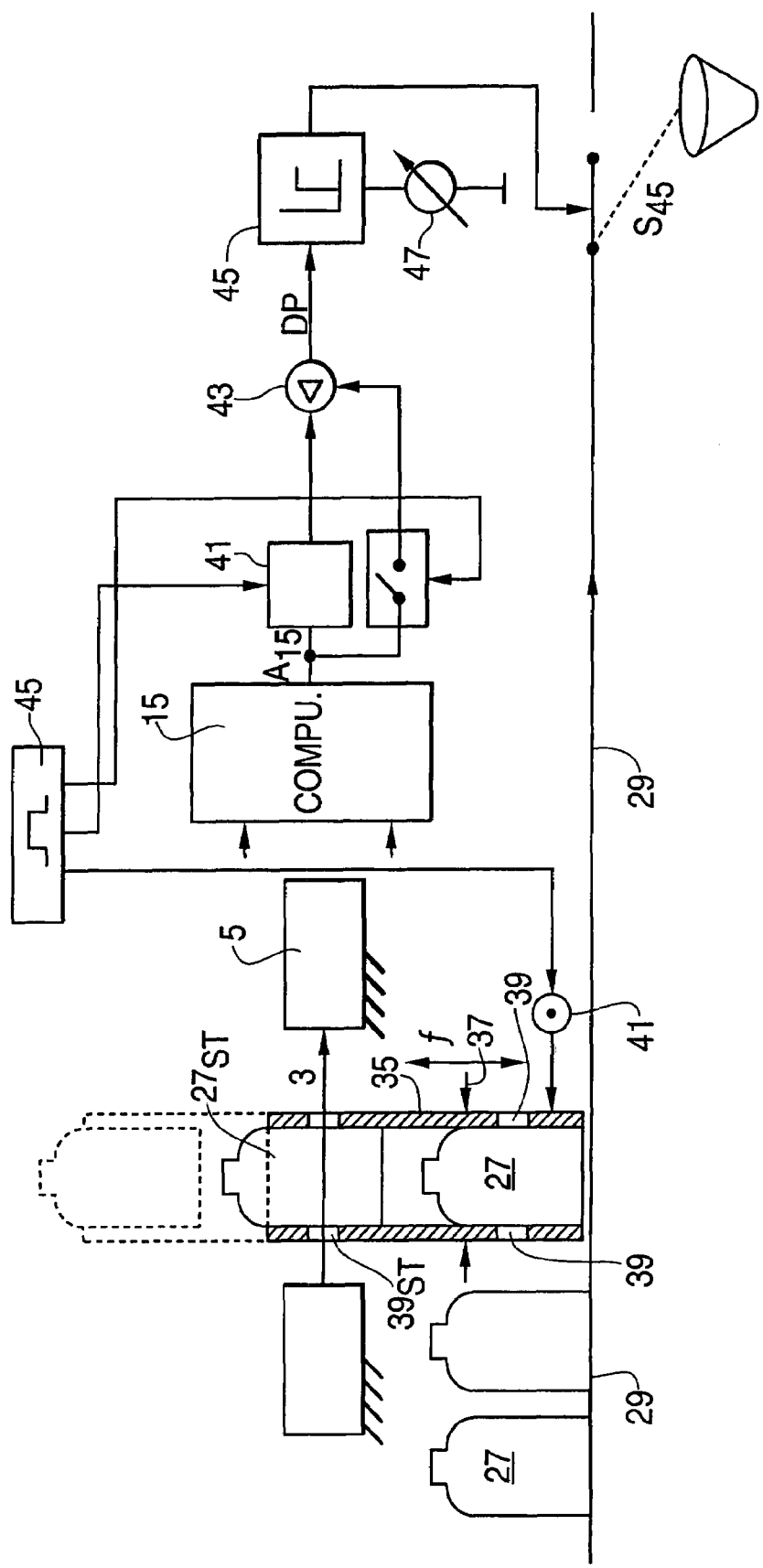

The invention shall now be described by way of examples and with the help of figures. The figures show:

FIG. 1 simplified and schematically, an apparatus according to the present invention and performing the monitoring method according to the present invention;

FIG. 2 qualitatively over the wavelength axis, absorption lines of a gas species to explain wavelength modulation according to the present invention;

FIG. 3 the absorption spectra of a gas species as of oxygen at different pressures;

FIG. 4 qualitatively the spectrum of electric signals resulting from optoelectric conversion according to the present invention;

FIG. 5 qualitatively envelopes of spectra according to FIG. 4 at different pressures of gas species;

FIG. 6 qualitatively envelopes of the spectra according to FIG. 4 for different gas pressures defining for the caustic function;

FIG. 7 a representation in analogy to that of FIG. 6 for explaining determination of transition frequency with the help of the caustic function;

FIG. 8 schematically and qualitatively first filtering according to the present invention in one frequency area relative to the transition frequency as found according to FIG. 7;

FIG. 9 a simplified functional block diagram showing evaluation of filtering results according to FIG. 8;

FIG. 10 qualitatively an example of the course of an output signal of the embodiment of FIG. 9 as a function of pressure to be monitored;

FIG. 11 schematically by means of a signal flow/functional block diagram evaluation of a pressure indicative signal according to the present invention and with filtering according to FIG. 9;

FIG. 12 schematically and qualitatively second filtering according to the present invention in a second frequency area with respect to transition frequency determined according to FIG. 7;

FIG. 13 simplified, a functional block representation of performing filtering according to FIG. 12;

FIG. 14 qualitatively an example of the dependency of the output signal of the embodiment according to FIG. 13 from the pressure to be monitored;

FIG. 15 simplified and schematically by means of a signal flow/functional block diagram evaluating, a pressure indicative signal from the filtering according to FIG. 13;

FIG. 16 a further embodiment of the present invention, whereby filtering according to FIG. 8 and filtering according to FIG. 12 are exploited in combination;

FIG. 17 qualitatively, spectral envelopes of the spectra according to FIG. 4 for different pressure values for explaining tailoring the band pass filter according to FIG. 8;

FIG. 18 in a representation according to FIG. 17, tailoring band pass filter according to FIG. 12;

FIG. 19 again parameterized with the pressure, qualitatively spectral envelopes of spectra according to FIG. 4 under a second aspect of the invention for determining a transition frequency;

FIG. 20 in analogy to FIG. 8, tailoring first filtering in a frequency area above transition frequency as determined in FIG. 19;

FIG. 21 a representation in analogy to FIG. 9, thereby filtering according to FIG. 20;

FIG. 22 qualitatively an example of the dependency of output signal of embodiment according to FIG. 21 from gas pressure;

FIG. 23 in analogy to FIG. 11 evaluation of the result of filtering according to FIG. 21 for generating a pressure indicative signal;

FIG. 24 in analogy to FIG. 12 a representation of second filtering in a frequency area below transition frequency determined according to FIG. 19;

FIG. 25 in analogy to FIG. 13 a simplified functional block diagram for performing filtering according to FIG. 24;

FIG. 26 in analogy to FIG. 15, in a simplified form and by a functional block/signal flow diagram evaluating filtering according to FIG. 25 for generating a pressure indicative signal;

FIG. 27 qualitatively, an example of the dependency of output signal of the embodiment of FIG. 25 from pressure;

FIG. 28 a further embodiment according to the present invention and based on transition frequency as determined according to FIG. 19, thereby combining filtering according to FIGS. 20 and 24 for evaluating a pressure indicative signal;

FIG. 29 schematically and simplified, a twin-parallel measuring channel embodiment according to the present invention;

FIG. 30 the result of monitoring oxygen pressure with the embodiment according to FIG. 29 in one pressure range;

FIG. 31 in a representation according to FIG. 30, the results in a second pressure range;

FIG. 32 in a representation according to the FIGS. 30 and 31, the results when monitoring over a larger pressure range;

FIG. 33 a functional block/signal flow diagram of a part of an evaluation unit according to the present invention exploiting signal courses as e.g. shown in FIG. 32;

FIG. 34 most simplified, an apparatus according to the present invention and operating according to the method of the present invention for testing transparent closed containers in a stream with respect to gas content;

FIG. 35 a simplified signal flow/functional block diagram of an evaluation unit in a further variant, and FIG. 36 a variant according to the present invention of the apparatus according to FIG. 34.

In FIG. 1 there is shown by means of a functional block diagram the generic structure of a monitoring system according to the present invention for monitoring pressure of a gas. The system comprises a laser arrangement 1 generating a laser beam B transmitted through a specimen 3 of gas containing the gas species to be pressure monitored. The laser beam B as transmitted through the specimen 3 is received at an optical input of an optoelectric converter arrangement 5 and is converted in an electric signal $S_5$ which is operationally connected to the input $E_7$ of an evaluation unit 7. The output signal $S_7$ at output $A_7$ of evaluation unit 7 is a pressure indicative signal indicative of the pressure of the gas species in specimen 3.

The laser arrangement 1 is modulatable with respect to $\lambda_L$ of the light of beam B. As schematically shown in FIG. 1 it may be considered having a wavelength control input M to which there is operationally connected a modulating generator 9. Generator 9 generates a periodic modulating signal to input M of laser arrangement 1 at a frequency $f_C$ and with a peak to peak level value $A_{pp}$. Thereby, the beam B having generically a wavelength $\lambda_L$ is wavelength-modulated with a frequency $f_C$ around the value $\lambda_{Lo}$ with a modulation hub H as a function of $A_{pp}$.

In FIG. 2 there is qualitatively shown absorption line $E_{abs}(G)$ of a gas species G to be monitored. The laser arrangement 1 is thereby wavelength-modulated so that the modulation hub H includes at least one of the absorption lines of the gas species, according to FIG. 2 e.g. just one absorption line.

In fact, the absorption line as schematically shown in FIG. 2 is an absorption spectrum as shown in FIG. 3. This FIG. shows as an example for a gas species to be pressure monitored, namely for oxygen, the absorption spectra for a pressure of 200 mbar (a), 75 mbar (b) and 40 mbar (c) of the specimen exclusively containing the gas species.

The absorption spectrum and its pressure dependency as exemplified for oxygen in FIG. 3 is with respect to its qualitative shape and behavior encountered for most gas species.

By modulating the wavelength of the laser beam B according to FIG. 1 and as shown in FIG. 2 and by transmitting the laser beam B through the gas specimen 3 as of FIG. 1 having the absorption spectrum as shown in FIG. 3, converted signal $S_5$ has a discrete energy spectrum as shown qualitatively in FIG. 4. There is a normally relatively high spectral line at zero frequency, as a DC component succeeded at rising frequency by a spectral line at modulation frequency $f_C$ of the laser beam and higher order frequencies of $f_C$. The discrete energy spectrum of signal $S_5$ defines for the spectrum envelope EN as shown for the example of gas specimen, namely oxygen, qualitatively in FIG. 4.

In FIG. 5 the pressure—p—dependency of the envelope EN, thus EN(p) is shown, whereby the envelope according to (a) accords with the 200 mbar absorption spectrum (a) of FIG. 3 and, accordingly, the envelopes (b) and (c) with the respective absorption spectra (b) and (c) of FIG. 3. It has to be noted that the spectra and respectively their envelopes EN(p) as shown in FIGS. 4 and 5 are shown with a logarithmic energy scaling on the vertical axis e.g. according to a logarithm of signal energy to noise energy in dB.

In FIG. 6 there is purely qualitatively shown a multitude of envelopes EN(p) parameterized by the pressure p of the gas species in specimen 3, whereby the arrow "$p_{increase}$" indicates the development of the envelopes as pressure p of the gas species increases. The collectivity of all the envelopes EN defines for a function course CA to which each of the collectivity of envelopes EN is a tangent. We call this function CA the caustic function.

The inventors of the present invention have investigated the behavior of signal $S_5$ in dependency of the pressure p of the gas species in specimen 3 of FIG. 1 and have found the spectral behavior in dependency of pressure as has been exemplified up to now here without a claim for scientific exactness.

This basic cognition has been exploited by the inventors in different manners as will be now further exemplified with the target to generate at the output of evaluation unit 7 as of FIG. 1 a pressure indicative signal $S_7$.

According to a first aspect of the present invention and as shown in FIG. 7 the inventors have recognized that whenever the pressure of the gas species is to be monitored up to maximum pressure $p_{max}$ a transition frequency $f_{Tmax}$ is important. If according to FIG. 6 the maximum pressure $p_{max}$ up to which the pressure p of the gas species shall be monitored is selected, now switching to FIG. 7, the locus where the envelope $EN(p_{max})$ touches the caustic function CA in the spectral representation defines for the addressed transition frequency $f_{Tmax}$. In both frequency areas, I above $f_{Tmax}$ and II below $T_{max}$ the pressure dependency of $S_5$ according to FIG. 1 is specific. Thereby, it has to be noted that the modulation frequency $f_C$ is practically always below $f_{Tmax}$, especially for selected maximum pressures $p_{max}$ as performed in practice. Thus, in a first embodiment the spectrum of $S_5$ is evaluated in the first addressed frequency area I to generate a pressure indicative signal.

It has to be noted that we speak generically of a frequency "area" if a one-side open frequency range is addressed and that we speak of a frequency "band" if a two-side closed frequency range is addressed.

According to FIG. 8 in one embodiment there is thus only evaluated the frequency area I, i.e. with a frequency $f_I$ $$F_{Tmax} \leq f_I$$

e.g. by providing a high-pass filter with the lower cut-off frequency not lower than the transition frequency $f_{Tmax}$.

Thus, the evaluation unit 7 as of FIG. 1 at least comprises, according to FIG. 9, a filter unit $F_I$ operating in the frequency area I as a low-pass filter with a lower cut-off frequency not lower than the transition frequency $f_{Tmax}$. An example of the pressure—p—dependency of the output signal $S_{FI}$ of filter $F_I$ up to the maximum pressure to be monitored $p_{max}$, is shown in FIG. 10, qualitatively. Energy and pressure are thereby linearly scaled in arbitrary units.

By prestoring a signal vs. pressure characteristic, as shown in FIG. 11 denoted as $S_{FIref}$ in a memory unit $11_I$, as e.g. in a look-up table unit, comparing the actual output signal $S_{FI}a$ of filter unit $F_I$ with such characteristic in a comparing unit $13_I$, the actual pressure value $p_a$ as shown in dashed lines in FIG. 10 is evaluated as a pressure indicative signal. This signal may directly be used as output signal $S_7$ of evaluation unit 7.

In a second embodiment of the invention and with an eye on FIG. 7, the lower frequency area II, which is actually a frequency band, is exploited. Thereby, filtering is performed as shown in FIG. 12 by a filter with an upper cut-off frequency not higher than the transition frequency $f_{Tmax}$ and with a lower cut-off frequency which is above the modulation frequency $f_C$ of the laser wavelength modulation. Thus, there is performed in this embodiment as a second possible filtering, band pass filtering with a characteristic having an upper cut-off frequency not higher than the transition frequency and a lower cut-off frequency above the modulation frequency $f_C$ of the periodic wavelength modulation.

In this embodiment and according to FIG. 13 the evaluation unit 7 comprises a filter unit $F_{II}$ providing for the filter characteristic according to FIG. 12, thereby generating an output signal $S_{FII}$ in dependency of which the pressure indicative signal $S_7$ is generated. Here too, signal $S_{FII}$ is already are per se pressure indicative.

In analogy to FIG. 10, FIG. 14 shows a qualitative dependency of output signal $S_{FII}$ from the pressure p of the gas species in specimen 3 of FIG. 1 to be monitored.

In complete analogy to FIG. 11 and according to FIG. 15 for generating a signal which is indicative of the actual pressure of the gas specimen, the characteristic $S_{FIIref}$ of output signal as of FIG. 14 is stored in a storing unit $11_{II}$, e.g. in form of a look-up table. This characteristic $S_{FIIref}$ is compared, as schematically shown by comparing unit $13_{II}$, with the actual signal $S_{FIIa}$, thereby generating at the output of comparing unit $13_{II}$ a signal according to the actual pressure value $p_a$ in dependency of which the pressure indicative signal $S_7$ is generated.

In a further embodiment, the embodiments according to the FIGS. 8 to 11 and of FIGS. 12 to 15 are combined. This is shown in FIG. 16 which only needs little additional explanation in view of the explanations given to the respective single-filter embodiment. At the output of the respective comparing units $13_I$ and $13_{II}$ there appear signals which are both in fact indicative of the actually prevailing gas species pressure $p_a$ in the gas specimen being monitored. Nevertheless, and as addressed by the different shaping of the characteristics in FIGS. 10 and 14, the redundancy of having two output signals indicative of the same actual pressure value $p_a$ is exploited in a computing unit 15, principally to rise accuracy of pressure indication by the pressure indicative signal $S_7$.

Generically spoken as evaluation of both frequency areas I and II by according filtering leads to two different signal dependencies from pressure according to $S_{FI}$ and $S_{FII}$—these two characteristics may be different with respect e.g. to sensitivity (steepness of the characteristic), ambiguity, signal to noise ratio, etc.—it becomes possible to remedy the drawback of one characteristic, e.g. ambiguity, by the advantage of the second characteristic, e.g. unambiguity, thereby maintaining the advantage of the first characteristic, e.g. high sensitivity, without making use of the drawbacks of the second characteristic, e.g. low sensitivity. Thus, principally by exploiting filtering measurements in the two frequency areas—above and below the transition frequency $f_{Tmax}$—high flexibility is gained to generate an accurate pressure indicative signal with desired characteristics, which will normally be high sensitivity, unambiguity and high signal to noise ratio.

Further and with an eye on filtering in the first frequency area I according to FIG. 8 and as shown in that figure with dashed-pointed lines, it is a variant to perform this first filtering as band pass filtering. The reason why this is considered may be seen in FIG. 6. As the envelope EN according to the selected maximum pressure $p_{max}$ crosses the zero line as at point N of FIG. 6, noise energy becomes predominant. Therefore, by performing band pass filtering in frequency area I, noise energy in the signal $S_{FI}$ is reduced.

Further, and especially with an eye on combining the filtering in the first frequency area I with filtering in the second area II according to the embodiment of FIG. 16, separation of the two filters is reached by performing first filtering $F_I$ with a lower cut-off frequency $f_{I-}$ higher than the transition frequency $f_{Tmax}$ as shown in FIG. 8 and/or to perform the second filtering $F_{II}$ as shown in dashed line in FIG. 12 with an upper cut-off frequency $f_{II+}$ at a frequency below the transition frequency $f_{Tmax}$.

Whenever first filtering comprises band pass filtering in a frequency band $BP_I$ of FIG. 8, there remains still a degree of freedom, where the center frequency $f_{ZI}$ of this band pass filtering shall be established.

FIG. 17 shows a representation according to FIG. 6. When considering in the spectral representation in frequency area I, the energy in signal $S_{FI}$ at a frequency f is in fact given, in dependency of pressure p, by the infinitesimal surface area as shown in hatched representation in FIG. 17. Therefore, it might be seen that at a prevailing pressure p this energy is proportional to the prevailing spectral amplitude at frequency f, with respect to envelope EN(p). Sensitivity is thereby given by the derivative of that spectral amplitude vs. pressure. It has further to be noted (logarithmic scale) that whenever a pressure-dependent spectral envelope EN(p) reaches zero dB line, the noise energy in signal $S_5$ becomes equal to the signal energy therein, i.e. below that zero dB line, the noise energy becomes predominant. Therefore, it is one rule to find the central frequency $f_{ZI}$ of band pass filtering in frequency area I, to establish a desired characteristic of derivative of spectral amplitude vs. pressure and to select as the addressed central frequency $f_{ZI}$ of FIG. 8 that frequency f where this derivative accords at least approximately with the desired characteristic. Thereby, it has to be noted that a maximum derivative vs. pressure leads to maximum sensitivity. Because the characteristic of spectral amplitude vs. pressure at a given frequency f is not linear, one may e.g. select where, i.e. in which pressure range, maximum sensitivity shall be reached, in other words in which pressure range maximum sensitivity shall be realized.

Thereby, signal to noise ratio may be an additional target value. Is is dependent on the bandwidth $BP_I$ of band pass filtering in frequency area I. The larger the bandwidth $BP_I$ is selected, the smaller will be, as a generic rule, sensitivity in that the derivative of signal energy vs. pressure will be decreased, but, on the other hand, the larger will be the signal to noise ratio. This becomes evident when again considering FIG. 17, where a filter frequency band $BP_I$ has been drawn in dashed line. The derivative of spectral energy of the signal $S_{FI}$ is represented by the spectral surface area hatched under $BP_I$, the derivative of which vs. pressure becoming smaller with increasing bandwidth $BP_I$, the noise energy represented by the surface area under $BP_I$ below zero dB becoming relatively smaller with increasing bandwidth.

Therefore, one approach to select central frequency $f_{ZI}$ under consideration of signal to noise ratio is to loop one or more than one time through the steps of
a) determining the central band pass filtering frequency $f_{ZI}$ by finding that frequency f at which the derivative of spectral amplitude vs. pressure accords best with the desired characteristic;
b) selecting bandwidth $BP_1$ with respect to the central frequency found additionally considering signal to noise ratio and sensitivity, possibly readjusting center frequency and bandwidth with the target of realizing a desired optimum compromise between sensitivity and signal to noise ratio.

We have now described how filtering in frequency area I may be realized. Let's turn now to considerations about filtering in frequency area II.

As was explained in context with FIG. 12, filtering in frequency range II is performed by band pass filtering with an upper cut-off frequency $f_{II+}$ at most at $f_{Tmax}$ and with a lower cut-off frequency $f_{II-}$ above modulation frequency $f_C$ of laser wavelength modulation.

According to FIG. 18 and with an eye on selecting central frequency of band pass filtering, the same considerations prevail as were explained in context with FIG. 17 for band pass filtering in the frequency area I. That is, and with an eye on FIGS. 18 and 12, the central frequency $f_{ZII}$ is selected by finding the frequency f whereat the derivative of spectral amplitude vs. pressure at least approximately accords with a desired characteristic. Thereby, additionally and with respect to selecting frequency band $BP_{II}$ of band pass filtering $F_{II}$ signal to noise ratio is considered, although being less critical as becomes evident from FIG. 18 than in the frequency area I. Again, with sensitivity to be reached as one target function and signal to noise ratio as a second target function the steps of
a) determining the center frequency $f_{ZII}$ of filter $F_{II}$ is performed by establishing where the derivative of spectral amplitude vs. pressure of the signal $S_{FII}$ (FIG. 13) at least approximately accords with a desired characteristic and
b) tailoring bandwidth $BP_{II}$ for a desired signal to noise ratio are performed once or more than one time in a looping manner.

We have now described the present invention under the aspect of having an upper maximum pressure $p_{max}$ established up to which the pressure of the gas species shall be monitored.

Let's now consider a further aspect, where there is established a pressure range between a maximum pressure $p_{max}$ and a minimum pressure $p_{min}$ in which the pressure of the gas species shall be monitored according to the invention.

Thereby, FIGS. 1 to 5 still prevail as well as the explanations which were given in context with these figures.

FIG. 19 shows a representation in analogy to FIG. 6. It shows the spectral envelope for the maximum pressure to be monitored $EN(p_{max})$ as well as the spectral envelope for minimum pressure to be monitored $EN(p_{min})$. Thus, the pressure range $\Delta p$ inclusive the limit values at $p_{max}$ and $p_{min}$ shall be monitored. In this case there is determined a transition frequency $f_{T\Delta p}$ there, where the envelope $EN(p_{min})$ crosses the spectral envelope $EN(p_{max})$. In analogy to $f_{Tmax}$ this transition frequency $f_{T\Delta p}$ delimitates two frequency areas $I_{\Delta p}$ and $II_{\Delta p}$.

In one embodiment and according to FIG. 20 there is performed in the frequency area $I_{\Delta p}$ filtering as of high-pass filtering with a lower cut-off frequency $f_{\Delta pI-}$ which is not lower than the transition frequency $f_{T\Delta p}$. This results in an embodiment of the present invention according to FIG. 21 having a filter $F_{\Delta pI}$ operating in the frequency area $I_{\Delta p}$ of FIG. 19 as a high pass filter. The pressure indicative signal $S_7$ of evaluation unit 7 depends on output signal of filter $F_{\Delta pI}$, $S_{FAI}$. There results as a qualitative example an output signal $S_{F\Delta pI}$ of filter $F_{\Delta pI}$, according to FIG. 22. Energy and pressure are thereby again linearly scaled in arbitrary units.

In FIG. 23 there is shown in analogy with FIG. 11 the structure of the evaluation unit 7 for evaluating the filter signal $S_{F\Delta pI}$ to generate a pressure indicative signal $S_7$. In view of the explanations given in context with FIG. 11, FIG. 23 and the respective embodiment becomes perfectly clear to the skilled artisan and needs no further explanation.

In a further embodiment of the invention and with an eye on FIG. 19 the lower frequency area $II_{\Delta p}$, which is again actually a frequency band, is exploited. Thereby, filtering is performed as shown in FIG. 24 by a filter with an upper cut-off frequency $S_{\Delta pII+}$ not higher than the transition frequency $f_{T\Delta p}$ and with a lower cut-off frequency $S_{\Delta pII-}$ which is above the modulation frequency $f_C$ of the laser wavelength modulation.

In this embodiment and according to FIG. 25 the evaluation unit comprises in analogy to the embodiment as shown in FIG. 13 a filter unit $F_{\Delta pII}$ providing for the filter characteristic according to FIG. 24, thereby generating an output signal $S_{F\Delta pII}$, in dependency of which the pressure indicative signal $S_7$ is generated. Again the signal $S_{F\Delta pII}$ is per se pressure indicative.

In analogy to FIG. 15, FIG. 26 shows the structure of the evaluation unit 7 exploiting the output signal $S_{F\Delta pII}$ of filter $F_{\Delta pII}$ to establish for the pressure indicative signal $S_7$. Here too, no additional explanations are necessary for the skilled artisan. Further, FIG. 27 shows in analogy to FIG. 14 quantitatively an example of the dependency of output signal $S_{F\Delta pII}$ from the pressure p of the gas species in specimen 3 of FIG. 1 being between the minimum and maximum pressures $p_{min}$ and $p_{max}$.

In FIG. 28 a further embodiment is shown combining the embodiment as exemplified and explained with the help of the FIGS. 20 to 23 with the embodiment as explained in context with the FIGS. 24 to 27. The target of combining these embodiments is the same as was discussed in context with the combined embodiment of FIG. 16. In view of FIG. 16 and the explanations given thereto the embodiment of FIG. 28 needs no additional explanations for the skilled artisan.

With an eye on FIG. 8 and the explanations given thereto also in the case of providing filtering in the frequency area $I_{\Delta p}$ according to FIG. 20, and as shown in dashed-dotted lines, band pass filtering is applied. Further, again based on the explanations given in context with FIG. 8, in one embodiment, especially in the embodiment making use of filtering in both frequency areas $I_{\Delta p}$ and $II_{\Delta p}$, the lower cut-off frequency $f_{\Delta pI-}$ of filtering in the frequency ares $I_{\Delta p}$ is higher than the transition frequency $f_{T\Delta p}$. Further, and referring to FIG. 12 and the explanations thereto, in a further variant according to FIG. 24 the upper cut-off frequency $f_{\Delta pII+}$ is selected below the transition frequency $f_{T\Delta p}$.

In spite of the fact that, with an eye on FIGS. 19 and 20, band pass filtering $F_{FpI}$ in frequency area $I_{\Delta p}$ may be performed with respect to selecting central frequency $f_{Z?pI}$ and bandwidth, under considerations similar to those given in context with FIGS. 17 and 18, it is of prime importance here that such band filtering is established between the transition frequency $f_{T\Delta p}$ and a noise limit frequency $f_N$ (see FIG. 19) where at $p_{min}$ the noise energy in signal $S_5$ equals signal energy therein. Thereby, such band pass filtering may be performed so that the energy difference in the spectrum between the envelope $EN(p_{max})$ and the envelope $EN(p_{min})$ becomes maximum.

It has to be noted that, as was mentioned, the spectral envelopes EN(p) as shown in the various figures are merely qualitative. Nevertheless, in FIG. 19 a bandwidth $BP_{\Delta pI}$ is arbitrarily shown with the hatched surface representing the addressed energy difference.

Principally band pass filtering in frequency area $I_{\Delta p}$ is performed by respective selection of center frequency $f_{Z\Delta pI}$ (see FIG. 20) and bandwidth $BP_{\Delta pI}$ under the constraint that noise energy of the output signal $S_5$ where the filtering is effective is at most equal to signal energy at maximum pressure to be evaluated.

Considering frequency area $II_{\Delta p}$ and with an eye on FIG. 24 band pass filtering is performed with a lower cut-off frequency $f_{\Delta pII-}$ above modulation frequency $f_e$ of the periodic wavelength modulation and with an upper cut-off frequency $f_{\Delta pII+}$ which is at most equal to the transition frequency $f_{T\Delta p}$. Again with an eye on FIG. 19 the central frequency and the bandwidth of this filtering is selected so as to perform band pass filtering there, where the energy difference in the envelope spectrum of signal $S_5$ between applying the maximum pressure to be monitored $p_{max}$ and the minimum pressure $p_{min}$ to be monitored to become maximum. The respective energy difference to be considered is shown in FIG. 19 in frequency area $f_{II\Delta p}$ in hatched representation.

We have shown embodiments for evaluating pressure indicative signals making use of single filtering above or below of a transition frequency $f_{Tmax}$ and $f_{T\Delta p}$ respectively or to combine filtering in two parallel channels, thereby performing filtering in both frequency areas above and below the respective transition frequency $f_{Tmax}$, $f_{T\Delta p}$. Thus, in the latter embodiment and as shown in FIG. 29 at least two, namely a first monitoring channel $K_I$ and a second monitoring channel $K_{II}$, are formed with filtering $F_I$ and $F_{II}$, respectively tailored in dependency on how transition frequency $f_T$ has been defined. Thus, FIG. 29 is an embodiment as of FIG. 16 or 28.

Thus, dependent on the output signal of the respective first and second filtering $F_I$, $F_{II}$ in the respective channels $K_I$ and $K_{II}$ the pressure indicative signal is computed.

Thereby, there is exploited that the result of the respective first and second filtering in the channels $K_I$ and $K_{II}$ becomes different. I.e. the output of filter $F_I$ varies as a function of the pressure of the gas species to be monitored differently than the result of the second filtering $F_{II}$.

In FIG. 30 there is shown the result of monitoring pressure of a gas specimen, thereby of oxygen as an example, by showing the output signal $S_{FI}$ and $S_{FI}$ of filtering in the respective channels $K_I$ and $K_{II}$ as of FIG. 29. The signals $S_{FI,II}$ are scaled in arbitrary but equal units.

For filtering in frequency area I a band pass filter is used. The filters are not optimized with respect to sensitivity and signal to noise ratio. The lower cut-off frequency of band pass filter in channel $K_I$ as well as upper cut-off frequency of band pass filter in channel $K_{II}$ are nevertheless selected so as to be clearly distant from both transitions frequencies $f_{Tmax}$ and $f_{T\Delta p}$.

It may be seen that there is generated a first output signal $S_{FI}$ of first filtering which has in the pressure subrange $\Delta p_s$ of about 0 mbar to 50 mbar out of the overall monitored pressure range $\Delta p$ of about 0 mbar to 75 mbar a derivative vs. pressure, the absolute value of which being larger than the absolute value of the derivative vs. pressure characteristic of the signal $S_{FII}$, i.e. of filtering in channel $K_{II}$. In FIG. 31 there is shown in a representation analog to that of FIG. 30 the respective output signals $S_{FI}$ and $S_{FII}$ of the respective channel filtering in a different range of pressure, again as an example of oxygen pressure, namely in the range of about 75 to 200 mbar. From FIG. 31 it might be seen that here within the pressure subrange $\Delta p_s$ of about 110 to 190 mbar the absolute value of the derivative of signal $S_{FI}$ vs. pressure is larger than such derivative of the signal $S_{FII}$. Thus, one can say that in a two-channel approach according to FIG. 29 there is generated by first filtering $F_I$ a first signal with a first derivative vs. pressure in a predetermined pressure range $\Delta p$ and by means of second filtering $F_{II}$ a signal with a second derivative vs. pressure in the predetermined pressure range $\Delta p$, whereby absolute values of one of the derivatives is smaller than absolute values of the other derivatives in at least one pressure subrange $\Delta p_s$ within the predetermined pressure range $\Delta p$. Thereby, the derivatives are considered without taking noise into account, i.e. by smoothening the respective output signals, because noise would provide for random derivatives vs. pressure characteristics.

FIG. 32 shows in a representation in analogy to that of FIGS. 30 and 31 the course of signal $SF_I$ and at $S_{FII}$ at a predetermined pressure range to be monitored of about 0 to 195 mbar. Therefrom, it might be seen that first filtering $F_I$ in channel $K_I$ which accords to filtering in the frequency area I above transition frequency $f_{Tmax}$ or $f_{T\Delta p}$ has derivatives vs. pressure which are exclusively positive in pressure subrange $\Delta p_{S1}$ and exclusively negative in a second pressure subrange $\Delta p_{S2}$ out of the overall predetermined pressure range $\Delta p$. Further, the derivatives of the second signal $S_{FII}$ are exclusively of one signum in the overall pressure range $\Delta p$.

Further, the absolute values of the derivatives of the first signal $S_{FI}$ are larger at least in the subrange $\Delta p_{S1}$, thereby again not considering noise.

The signal as shown in the FIGS. 30 to 32 are typical for gases and respective filtering in the two frequency areas above and below transition frequency.

The results as shown have been monitored on oxygen gas.

With an eye on the signal courses of FIG. 32 in the pressure range $\Delta p$ to be monitored it is evident that the signal $S_{FI}$ has a sensitivity in the pressure subranges $\Delta p_{S1}$ and $\Delta p_{S2}$ which is larger than the sensitivity of signal $S_{FI}$ in the respective pressure subranges. On the other hand the signal $S_{FI}$ is ambiguous in that one signal value of $S_{FI}$ may be indicative for two pressure values which are highly different. For instance and as shown in FIG. 32 a signal value $S_o$ of signal $S_{FI}$ may be indicative for a pressure of about 25 mbar, but also for a pressure of about 170 mbar.

Although having a smaller sensitivity, signal $S_{FII}$ is not ambiguous over the range $\Delta p$ including the subranges $\Delta p_{S1}$ and $\Delta p_{S2}$.

Thus, in one embodiment of signal computing as by unit 15 of FIG. 29 the following may be done, according to FIG. 33:

Principally from a signal dependent on the second signal $S_{FII}$ from channel $K_{II}$ according to FIG. 29, which accords with filtering results in frequency area II, the prevailing pressure subrange for the instantaneously prevailing result of first filtering, $S_{FI}$, is determined. As schematically shown in FIG. 33 the prevailing actual signal $S_{FII}$ is compared with the prestored reference characteristic $S_{FIIref}$ in unit $11_{II}$ by comparing unit $13_{II}$. The comparison result at the non-ambiguous characteristic $S_{FIIref}$ is indicative for an estimate pressure value $p_e$ and is fed to a comparator unit 20. There the estimate pressure value $p_e$, i.e. the signal indicative for that value, is compared with limit values for the pressure subranges $\Delta p_S$, according to $\Delta p_{S1}$ and $\Delta p_{S2}$ of FIG. 32. The result of this comparison is an output signal which is indicative of the pressure subrange $\Delta p_S$, namely with an eye on FIG. 32 of either $\Delta p_{S1}$ or $\Delta p_{S2}$.

The output signal of comparator unit 20 controls via a control input $C_{21}$ the activation of either a storage unit 23a or 23b both being e.g. look-up tables. In the one storage unit 23a the characteristic $S_{FIref}$ of the output signal of first filtering $F_I$ in the first pressure subrange according to $\Delta p_{S1}$ as of FIG. 32 is prestored, whereas in storage unit 23b again e.g. in the form of a look-up table, the characteristic $S_{FIref}$ of the result of first filtering $F_I$ in the pressure subrange $\Delta p_{S2}$ is prestored.

The pressure subrange indicative signal $\Delta p_S$ controls which of the two prestored characteristics is compared in a further comparator unit 25 with the prevailing result signal $S_{FI}$ of first filtering $F_I$. This is schematically shown in FIG. 33 by a controlled selection unit unit 27.

Thus, after having determined from a signal which depends on second filtering $F_{II}$ the prevailing pressure subrange $\Delta p_S$ from a signal which depends on the result of first filtering, $F_I$ in the subrange $\Delta p_S$ the pressure indicative signal is established.

Before proceeding to describing further embodiments of the invention practically established dimension indications shall be given which have been used for oxygen pressure monitoring:

Center frequency $f_{ZII}$ of second band pass filter $F_{II}$ relative to modulation frequency $f_c$:

$$10 \leq f_{ZII}/f_c \leq 20$$

Center frequency $f_{ZI}$ of first band pass filter $F_I$:

$$50 \leq f_{ZI}/f_c \leq 120$$

Bandwidth of second band pass filter $BP_{II}$:

$$1 \leq B_{II}/f_c \leq 18$$

Bandwidth of first band pass filter $B_I$:

$$50 \leq B_I/f_c \leq 1000$$

Wavelength derivation H according to FIG. 1 of laser modulation at least 5 pm, thereby preferably:

$$50 \text{ pm} \leq H \leq 500 \text{ pm}$$

Thereby, as a modulatable laser a Vertical Cavity Surface Emitting Laser was used, modulated at $f_c \approx 800$ Hz.

The invention with all different embodiments described up to now is, in a further embodiment, applied in a practical system as will now be described, whereby further embodiments shall be addressed.

In FIG. 34 there is schematically shown a system for monitoring pressure of a gas species in closed containers which are transparent to the laser light as was described in the modulated wavelength band and which may be filled or not. Such containers, wherein the oxygen pressure has to be accurately monitored, are e.g. vials of glass or plastic containing a filling material which is not to be exposed to oxygen.

Thus, in a further embodiment of the present invention the gas species to be monitored is within a closed and transparent container, transparent to the light of the laser as applied. According to FIG. 34 such containers as e.g. glass or plastic material vials 27 are conveyed after having been filled and sealingly closed and possibly stored during shorter or longer time spans in atmospheric air, by means of a conveyor arrangement 29 as e.g. a carousel conveyor towards a gas pressure, specifically an oxygen pressure, monitoring station 31. Therein and according to FIG. 1 there is provided laser arrangement 1 modulatable as was described by means of modulating generator 9. The wavelength modulated laser beam B enters after having passed a container 27 under test as transmitted beam $B_{Tr}$ receiver unit 29 with optoelectric converter 5 according to FIG. 1 and subsequent evaluation unit 7. Depending on the construction of the system the container 27 under test continues to be conveyed by conveyor 29 during gas pressure monitoring, whereby in this case laser arrangement 1 and receiver unit 29 are moved along a predetermined trajectory path in synchronism with the conveyed container 27 under monitoring test.

Otherwise, in another construction, the container 27 under test is stopped so that the laser arrangement 1 and receiver arrangement 29 may be stationary.

The energy of the transmitted laser beam $B_{Tr}$ may thereby be influenced by the prevailing transparency of the overall transmission path in fact between laser arrangement 1 and optical input port of receiver unit 29, thereby especially by varying transparency of the container, be it due to tolerances of container material, of container wall contamination etc.

This is taken into account in that there is generically performed a transmission indicative measurement. As transmission influences the energy of the signals which were described to be filtered as well as significance of reference characteristics as in look-up tables with which actual filtering results are compared, the transmission indicative signal is applied for weighing such signals.

In spite of the fact that a prevailing transparency in the transmittance path 3 according to FIG. 1 may be measured as by making use of a separate laser beam, in one embodiment the laser beam B itself is exploited to provide also for the transparency indicative information. With an eye on FIG. 4 it was explained that the spectrum of signal $S_5$ contains the distinct spectral line at the modulation frequency $f_C$. Dependent on how wavelength modulation of the laser beam is realized, the spectral component at $f_C$ will be of higher or lower energy. When making use e.g. of a Vertical Cavity Surface Emitting Laser (VCSEL), where the center wavelength of emission spectrum is tunable and thus modulatable by amplitude modulating the forward current as is taught in H. P. Zappe et al. "Narrow-linewidth vertical-cavity surface-emitting lasers for oxygen detection", Appl. Opt. 39 (15), 2475-2479 (May 2000), the energy of the transmitted laser beam at frequency $f_C$ is quite large. Therefrom results that the energy of the signal $S_5$ is per se indicative of transmission. As has been explained in all filtering modes for evaluating the pressure indicative information in signal $S_5$ the energy at the frequency $f_C$ is not considered by selecting all filtering with a lowest-most cut-off frequency above the modulation frequency $f_C$.

According to FIG. 35 there is therefore provided a third channel $K_{CAL}$ as a calibration channel, whereat directly or possibly and as shown in dashed line via selective band pass filtering at frequency $f_C$, a transmission indicative signal $S_{Tr}$ is generated. This transmission indicative signal is used generically for weighing signals from which the pressure indicative signal depends. In the embodiments as were described and according to FIG. 35, whereat the filtering result signals $S_{FI}$ and $S_{FII}$ are used to find the according pressure-dependent value in look-up tables $11_I$ and $11_{II}$, irrespective which transition frequency $f_{Tmax}$ or $f_{T\Delta p}$ has been selected, the transmission indicative signal $S_{Tr}$ is applied to calibration units 33 which are provided at the output of the look-up table units $11_I$, $11_{II}$ as well as at the outputs of the filtering units $F_I$ and $F_{II}$.

Thus, the output signals which appear at the outputs of the respective comparing units 13 become independent from the instantaneously prevailing transmission characteristics of the transmission path 3 according to FIG. 1 and with an eye on FIG. 34 independent of possibly varying transmission of containers 27 which are monitored in line, i.e. in a stream of subsequent containers, with respect to the pressure of a specific gas species contained therein, as was addressed, especially of oxygen.

Still a further embodiment comprises to perform the gas species pressure monitoring as was described up to now upon such gas specimen which has a predetermined known pressure, be it for checking purposes of the overall functioning and of accuracy of the system as described, be it for providing a reference pressure indicative signal on the gas species under test. With an eye on the teaching of FIG. 34 providing for such standard monitoring may be done always after a predetermined number of containers 27 have been tested and may even be done before each of the containers 27 is monitored on prevailing gas species, in the present case on oxygen.

In FIG. 35 there is shown one embodiment for performing a standard or reference monitoring as was just addressed before gas species pressure monitoring at each of the containers 27.

According to FIG. 36 each container 27 to be tested and once conveyed by conveyor 29 into the monitoring station 31 according to FIG. 34 is gripped by a transfer member 35. The transfer member 35 may comprise a tubular member as shown with controlled gripping arrangement 37 and with a laser transition pass through 39. The transfer member 35 is movable perpendicularly to the path of conveyor 29 up and down as shown by the double-arrow F, thereby driven in a controlled manner by a drive 41. The laser arrangement 1 and the optoelectric converter arrangement 5 are located above the conveyor 29, so that whenever a container 27 to be tested is gripped in the position as shown, and is then lifted by means of drive 41 and member 35 in a monitoring position where the pass-through 39 opens the transition path for laser beam B. In FIG. 36 the transfer member 35 is shown in its lowered position, where the next container 27 to be tested is about to be gripped. The transfer member 35 further holds a standard or reference container $27_{ST}$, wherein a predetermined amount of the gas species to be monitored is present, resulting in a predetermined pressure at a given temperature. The standard container $27_{ST}$ within transfer member 35 is only rarely replaced. Together with transfer member 35 it is moved by means of controlled drive 41 up and down and as a second pass-through $39_{ST}$ is provided in transfer member 35 at a position according to the mounting position of standard container $27_{ST}$, whenever the transfer member 35 is in the position as shown in FIG. 36, the laser beam B transits through the standard container $27_{ST}$. Thereby, reference monitoring is performed. In dashed line FIG. 36 shows the position of standard container $27_{ST}$ whenever container 27 to be monitored is lifted in monitoring position.

Due to the fact that the pressure of a gas species in the closed containers is dependent on the temperature which is substantially equal, as given by the surrounding, for the containers to be tested and for standard container $27_{ST}$ within transfer member 35, the gas species contained within standard container $27_{ST}$ will be subjected to pressure variations due to the same temperature variations as the gas species possibly contained in the containers 27 to be tested. According to FIG. 36 after optoelectric conversion of the transmitted laser beam B signal processing is performed as was largely explained up to now finally at the signal computing unit 15. The signal generated at the output $A_{15}$ of computing unit 15 represents, as was explained, a signal which is indicative of the pressure of the specific gas species as momentarily monitored. As shown in FIG. 36, the standard or reference container $27_{ST}$ is also gas pressure monitored, and the result at the output $A_{15}$ is stored in a storing unit 41. Then the subsequent monitoring test result, which is generated at a container 27 to be tested, is fed to a difference forming unit 43 together with the stored reference result value in storing unit 41. Therefore, an output signal $D_p$ at the output of difference unit 43 is generated, which is indicative of the difference between the gas pressure indicative signal as monitored at the reference or standard container $27_{ST}$ and the next prevailing conveyed container 27 to be test monitored.

A time control unit 45 controls, as schematically shown in FIG. 35, storing of the output signal of unit 15 in storage unit 41, applying the prevailing output signal of unit 15 together with the stored reference signal to the difference unit 43 and up/down movement F of transfer member 35 via controlled drive 41.

Further, and as only schematically shown in FIG. 36, the resulting difference signal $D_p$ is fed to a threshold unit 45, where it is checked whether it reaches a predetermined threshold value or not, as preestablished by a threshold setting unit 47. Dependent on the comparison result of $D_p$ with the preset threshold value, the container 27 which is momentarily under test will be considered as fulfilling predetermined conditions with respect to the content of the gas species and will then be considered to be a closed, transparent container which holds at most a predetermined maximum amount of gas species, especially of oxygen, thus being a regular container. Those containers, which do not fulfill the said conditions and thus have e.g. a too high amount of oxygen, are discarded as shown in FIG. 36 schematically with discarding switch $S_{45}$ controlled from threshold checking at threshold unit 45.

As a further embodiment the storage unit 41 is replaced by an averaging unit, whereat subsequent reference pressure indicative signals monitored at standard containers $27_{ST}$ are averaged and the averaged result is fed to the difference unit 43. Thereby, whenever the standard container $27_{ST}$ is corrupt for whatever reason, its monitoring will not abruptly change the averaging result and thus the prevailing difference result $D_p$ will still remain accurate for some containers 27, thereby not leading to containers 27 under test being erroneously considered as fulfilling the predetermined gas conditions or not. Thereby (not shown) whenever the monitoring result of a standard container $27_{ST}$ leaves a predetermined signal range, an alarm may be established informing about corruption of the standard container $27_{ST}$.

Further, FIGS. 34 and 35 show single test station embodiments. For increasing throughput of tested containers 27 more than one test station 31 may be provided, operating in parallel, so that the test cycle time is divided by the number of parallel test stations allowing for increased speed of conveying the containers 27 by means of conveyor 29.

By means of the disclosed technique for gas pressure monitoring, applied for testing oxygen content in glass or plastic vials, test cycle times lower than 0.3 sec. were reached, allowing to accordingly test containers in a stream and thereby to test every single container 27.

What is claimed is:

1. A method of manufacturing closed, filled containers transparent to laser light, the pressure of a gas species therein being known, comprising:
    manufacturing closed, filled containers transparent to said laser light;
    conveying said containers in one direction into a monitoring station;
    providing at least one reference container transparent to said laser light;
    providing differently than in said one direction said at least one reference container to be exposed to transmission of said laser light;
    exposing said containers in said monitoring station and said at least one reference container to said transmission of said laser light;
    periodically modulating the wavelength of said laser light during said transmission over a wavelength band including at least one absorption line of said gas species;
    optoelectronically converting, said periodically modulated and transmitted laser light, thereby generating a monitoring signal from transmission respectively through said containers and a reference signal from said transmission through said at least one reference container;
    generating an output signal in dependency of said monitoring signal and said reference signal, and
    evaluating said output signal as a signal indicative of pressure of said gas species prevailing in a respective one of said containers and assigning said pressure to said one container.

2. The method of claim 1, wherein said gas species is oxygen.

3. The method of claim 2, wherein said evaluating comprises averaging over time.

4. The method of claim 3, said at least one reference container containing a predetermined pressure of said gas species.

5. The method of claim 2, said at least one reference container containing a predetermined pressure of said gas species.

6. The method of claim 1, wherein said evaluating comprises averaging over time.

7. The method of claim 6, said at least one reference container containing a predetermined pressure of said gas species.

8. The method of claim 1, said at least one reference container containing a predetermined pressure of said gas species.

9. The method of claim 1, further comprising exposing repeatedly at least one reference container to said transmission of said laser light, thereby generating repeatedly reference signals, generating said reference signal comprising averaging said repeatedly generated reference signals.

10. The method of claim 9, generating said output signal comprising evaluating a difference signal dependent on said reference signal and said monitoring signal.

11. The method of claim 10, wherein said at least one reference container is moved in a direction perpendicular to said one direction to become exposed to said laser light.

12. The method of claim 9, wherein said at least one reference container is moved in a direction perpendicular to said one direction to become exposed to said laser light.

13. The method of claim 9, further comprising checking said pressure indicative signal on plausibility.

14. The method of claim 9, wherein said container is substantially of glass or of plastic material.

15. The method of claim 9, wherein said container is a vial.

16. The method of claim 1, wherein said generating said output signal includes evaluating a difference signal dependent on said reference signal and said monitoring signal.

17. The method of claim 16, wherein said at least one reference container is moved in a direction perpendicular to said one direction to become exposed to said laser light.

18. The method of claim 16, further comprising checking said pressure indicative signal on plausibility.

19. The method of claim 16, wherein said container is substantially of glass or of plastic material.

20. The method of claim 16, wherein said container is a vial.

21. The method of claim 1, wherein said at least one reference container is moved in a direction perpendicular to said one direction to become exposed to said laser light.

22. The method of claim 21, further comprising checking said pressure indicative signal on plausibility.

23. The method of claim 21, wherein said container is substantially of glass or of plastic material.

24. The method of claim 21, wherein said container is a vial.

25. The method of claim 1, further comprising checking said pressure indicative signal on plausibility.

26. The method of claim 25, wherein said container is substantially of glass or of plastic material.

27. The method of claim 25, wherein said container is a vial.

28. The method of claim 1, wherein said container is substantially of glass or of plastic material.

29. The method of claim 28, wherein said container is a vial.

30. The method of claim 1, wherein said container is a vial.

* * * * *